US005620999A

United States Patent [19]
Weier et al.

[11] Patent Number: 5,620,999
[45] Date of Patent: Apr. 15, 1997

[54] BENZENESULFONAMIDE SUBTITUTED IMIDAZOLYL COMPOUNDS FOR THE TREATMENT OF INFLAMMATION

[76] Inventors: Richard M. Weier, 240 Hickory Ct., Lake Bluff, Ill. 60044; Paul W. Collins, 1557 Hawthorne Pl., Deerfield, Ill. 60015; Michael A. Stealey, 502 Juniper Pkwy., Libertyville, Ill. 60048; Thomas E. Barta, 1133 Maple Ave. Apt. 3-W, Evanston, Ill. 60602

[21] Appl. No.: 281,903

[22] Filed: Jul. 28, 1994

[51] Int. Cl.⁶ .................... A61K 31/415; C07D 233/58; C07D 405/04
[52] U.S. Cl. .................. 514/398; 548/325.1; 548/325.5; 548/333.5; 548/334.5; 548/337.1; 548/338.1; 548/341.1; 548/342.5; 548/343.1; 548/343.5; 548/345.1; 548/342.1; 548/311.7; 548/315.4; 514/396; 514/397; 514/400
[58] Field of Search ................ 548/342.1, 343.5, 548/333.5, 325.1, 342.5, 343.1; 514/396, 398

[56] References Cited

U.S. PATENT DOCUMENTS

| | | | |
|---|---|---|---|
| 3,707,475 | 12/1972 | Lombardino | 260/309 |
| 3,901,908 | 8/1975 | Fitzi et al. | 260/309 |
| 4,175,127 | 11/1979 | Dender et al. | 424/263 |
| 4,188,397 | 2/1980 | Hill | 424/273 R |
| 4,372,964 | 2/1983 | Whitney | 424/273 R |
| 4,472,422 | 9/1984 | Whitney | 424/273 R |
| 4,503,065 | 3/1985 | Wilkerson | 514/396 |
| 4,576,958 | 3/1986 | Wexler | 514/400 |
| 4,686,231 | 8/1987 | Bender et al. | 514/333 |
| 4,822,805 | 4/1989 | Takasugi et al. | 514/341 |

FOREIGN PATENT DOCUMENTS

| | | |
|---|---|---|
| 8665565 | 11/1986 | Australia . |
| 032113 | 7/1981 | European Pat. Off. . |
| 044486 | 1/1982 | European Pat. Off. . |
| 372445 | 6/1990 | European Pat. Off. . |
| 561717 | 5/1975 | Germany . |
| 1381031 | 1/1975 | United Kingdom . |
| 94/15932 | 7/1994 | WIPO . |
| WO95/00501 | 1/1995 | WIPO . |

OTHER PUBLICATIONS

T. Hla and K. Nielson, *Proc. Natl. Acad. Sci, USA*, 89, 7384 Aug. (1992).
J. Masferrer, et al, *Proc. Natl. Acad.Sci, USA*, 89, 3917 May (1992).
E. Meade et al, *J. Biol. Chem.*, 268, 6610 Mar. (1993).
Futaki et al, *Prostaglandins*, 47, 55 Jan. (1994).
T. Sharpe et al, *J. Med. Chem.*, 28, 1188 (1985) (S).
H. Greenberg et al, *J. Org. Chem.*, 31, 3951 Dec. (1966).
T. van Es et al, *J. Chem. Soc.*, 1363 (1963) (S).
J. Lombardino et al, *J. Med. Chem.*, 17, 1182 (1974) (S).

*Primary Examiner*—Johann Richter
*Assistant Examiner*—Laura L. Stockton
*Attorney, Agent, or Firm*—Joseph W. Bulock

[57] ABSTRACT

A class of imidazolyl compounds is described for use in treating inflammation and inflammation-related disorders. Compounds of particular interest are defined by Formula II

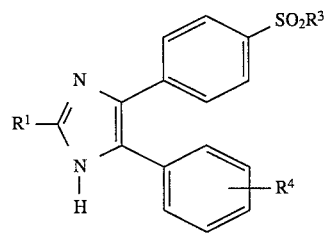

wherein $R^1$ is selected from lower alkyl, lower haloalkyl, lower hydroxyalkyl, lower aralkenyl, lower aryloxyalkyl, lower arylthioalkyl and heteroaryl; wherein $R^3$ is selected from lower alkyl and amino; and wherein $R^4$ is one or more radicals selected from hydrido, halo, lower alkyl and lower alkoxy; or where $R^4$ together with the phenyl radical forms naphthyl or benzodioxolyl; provided $R^1$ is not lower alkyl when $R^3$ is methyl and when $R^4$ is hydrido, methyl, methoxy or chloro; or a pharmaceutically-acceptable salt thereof.

23 Claims, No Drawings

1

BENZENESULFONAMIDE SUBTITUTED IMIDAZOLYL COMPOUNDS FOR THE TREATMENT OF INFLAMMATION

FIELD OF THE INVENTION

This invention is in the field of antiinflammatory pharmaceutical agents and specifically relates to compounds, compositions and methods for treating inflammation and inflammation-associated disorders, such as arthritis.

BACKGROUND OF THE INVENTION

Prostaglandins play a major role in the inflammation process and the inhibition of prostaglandin production, especially production of $PGG_2$, $PGH_2$ and $PGE_2$, has been a common target of antiinflammatory drug discovery. However, common non-steroidal antiinflammatory drugs (NSAIDs) that are active in reducing the prostaglandin-induced pain and swelling associated with the inflammation process are also active in affecting other prostaglandin-regulated processes not associated with the inflammation process. Thus, use of high doses of most common NSAIDs can produce severe side effects, including life threatening ulcers, that limit their therapeutic potential. An alternative to NSAIDs is the use of corticosteroids, which have even more drastic side effects, especially when long term therapy is involved.

Previous NSAIDs have been found to prevent the production of prostaglandins by inhibiting enzymes in the human arachidonic acid/prostaglandin pathway, including the enzyme cyclooxygenase (COX). Recently, the sequence of another heretofore unknown enzyme in the human arachidonic acid/prostaglandin pathway has been reported by T. Hla and K. Nielson, *Proc. Natl. Acad. Sci, USA*, 89, 7384 (1992) and named "cyclooxygenase II (COX II)" or "prostaglandin G/H synthase II". The discovery of an inducible enzyme associated with inflammation provides a viable target of inhibition which more effectively reduces inflammation and produces fewer and less drastic side effects. Cyclooxygenase II is inducible by cytokines or endotoxins and such induction is inhibited by glucocortoids (J. Masferrer, et al, *Proc. Natl. Acad. Sci, USA*, 89, 3917 (1992)). The 6-methoxy-2-napthylacetic acid metabolite of nabumetone has been found by E. Meade et al to selectively inhibit the COX II enzyme (*J. Biol. Chem.*, 268, 6610 (1993)). In addition, Futaki et al (*Prostaglandins*, 47, 55 (1994)) have reported that N-(2-cyclohexyloxy-4-nitrophenyl)methanesulfonamide inhibits the COX II enzyme.

The references below that describe antiinflammatory activity, show continuing efforts to find a safe and effective antiinflammatory agent. The novel imidazoles described herein are such safe and also effective antiinflammatory agents furthering such efforts. The invention compounds are found to show usefulness in vivo as antiinflammatory agents with minimal side effects. The substituted imidazolyl compounds described herein preferably selectively inhibit cyclooxygenase II over cyclooxygenase I.

U.S. Pat. No. 4,822,805, to Takasugi et al, describes pyridyl-imidazoles as antiinflammatory agents. Specifically, 2-[2-methoxy-4-(methylsulfonyl)phenyl]-4-methyl-5-(3pyridyl)imidazole is described.

U.S. Pat. No. 4,188,397, to Hill, describes 2,2-alkyldiylbis(thio)bis(imidazoles) with substituted phenyl radicals am the 4 and 5 positions of the imidazole rings as having antiinflammatory activity. Specifically, imidazoles having phenyl radicals substituted with methoxy, methylthio, trifluoromethylhalo and methylenedioxy are described.

T. Sharpe et al [*J. Med. Chem.*, 28, 1188 (1985)] describe antiarthritic activity of 4,5-diaryl-2-(substituted thio)-1H-imidazoles.

U.S. Pat. No. 4,686,231, to Bender et al, describes 4,5-diaryl-1H-imidazoles as inhibiting the 5-lipoxygenase pathway for the treatment of arthritis. 1-Methyl-4,5-bis(methoxyphenyl)-2-methylthio-1H-imidazole ms specifically described.

Australian publication AU8665565 describes cyano-2,2-bis(imidazoles) as having antihypertensive agents.

H. Greenberg et al [*J. Org. Chem.*, 31, 3951 (1966)] describe 4-(2-oxo-5-phenyl-4-imidazolin-4-yl)benzenesulfonamide in a study of the bromination reaction thereof.

T. van Es and O. Backeberg [*J. Chem. Soc.*, 1363 (1963)] describe the synthesis of [4,4'-imidazol-4,5-diyl]bis(benzenesulfonamide) for use in a study of substitution reactions on phenyl radicals.

European publication EP 372,445, published Jun. 13, 1990, describes 4,5-diaryl-1H-imidazoles as having antihypercholesterolemic activity. N-[[5-(4-Methylsulfonylphenyl)-4-phenyl-1H-imidazol-2-yl]thio]pentyl-N-octyl-N-heptylurea is specifically described.

U.S. Pat. No. 4,503,065, to Wilkerson, describes 4,5-diaryl-2-halo-1H-imidazoles as being antiinflammatory. Specifically, 1-(1-ethoxyethyl)-2-fluoro-4,5-bis(4-methylsulfonylphenyl)-1H-imidazole is described.

J. Lombardino (*J. Med. Chem.*, 17, 1182 (1974)) describes trisubstituted imidazoles as being antiinflammatory, and specifically 4,5-bis(4-methoxyphenyl)-2-trifluoromethyl-1H-imidazole. Similarly, U.S. Pat. No. 3,707,475, to Lombardino, describes antiinflammatory 4,5-diarylimidazoles. Specifically, 4-chlorophenyl-5-(4-methylthiophenyl)-2-trifluoromethyl-1H-imidazole is described.

U.S. Pat. No. 4,472,422, to Whitney, describes 4,5-diaryl-1H-imidazole-2-methanamines as having antiinflammatory activity. Specifically, 5-(4-fluorophenyl)-4-(4-methylsulfonylphenyl)-α,α-bis(trifluoromethyl)-1H-imidazole-2-methanamine is described.

U.S. Pat. No. 4,372,964, to Whitney, describes 4,5-diaryl-1H-imidazole-2-methanols as having antiinflammatory activity. Specifically, 5-(4-fluorophenyl)-4-(4-methylsulfonylphenyl)-α,α-bis(trifluoromethyl)-1H-imidazole-2-methanol is described. Additionally, Whitney describes 1-[4,5-diaryl-1H-imidazol-2-yl]-2,2,2-trifluoro-1-ethanones as having antiinflammatory activity. Specifically, 1-[5-(4-fluorophenyl)-4-(4-methylsulfonylphenyl)-1H-imidazol-2-yl]-2,2,2-trifluoro-1-ethanone is described.

U.S. Pat. No. 4,576,958, to Wexler, describes 4-phenyl-5-(4-methylsulfonylphenyl)-1H-imidazoles as having antiinflammatory activity. Specifically, 4-(4-fluorophenyl)-5-(4-methylsulfonylphenyl)-α,α-bis(trifluoromethyl-1H-imidazole-2-methanol and 4-(4-fluorophenyl)-5-4-methylsulfonylphenyl)-α,α-bis(trifluoromethyl-1H-imidazole-2-methanol, acetate is described.

U.S. Pat. No. 3,901,908, to Fitzi, et al, describes 2-alkyl-4,5-bis(substituted phenyl)-1H-imidazoles. Specifically, 2-tert-butyl-4-(4-methylsulfonylphenyl)-5-phenyl-1H-imidazole is described.

DESCRIPTION OF THE INVENTION

A class of substituted imidazolyl compounds useful in treating inflammation-related disorders is defined by Formula I:

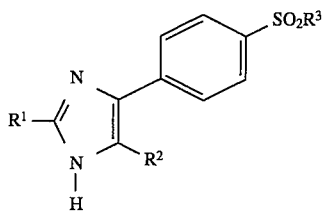

wherein $R^1$ is selected from alkyl, haloalkyl, aralkyl, heterocyclicalkyl, heteroaralkyl, acyl, cyano, alkoxy, alkylthio, alkylthioalkyl, alkylsulfonyl, haloalkylsulfonyl, arylsulfonyl, halo, hydroxyalkyl, alkylcarbonyl, arylcarbonyl, aralkylcarbonyl, cyanoalkyl, aralkenyl, aminoalkyl, alkylaminoalkyl, N-arylaminoalkyl, N-alkyl-N-arylaminoalkyl, carboxyalkyl, alkoxycarbonylalkyl, alkoxycarbonyl, haloalkylcarbonyl; carboxyl, alkoxyalkyl, aminocarbonyl, alkylaminocarbonyl, alkylaminocarbonylalkyl, heteroaralkoxyalkyl, heteroaryloxyalkyl, heteroarylthioalkyl, heteroarylalkylthioalkyl, aralkoxy, aralkylthio, heteroaralkoxy, heteroaralkylthio, heteroaryloxy, heteroarylthio, arylthioalkyl, aryloxyalkyl, haloaryloxyalkyl, arylthio, aryloxy, aralkylthioalkyl, aralkoxyalkyl, alkoxyaralkoxyalkyl, aryl and heteroaryl, wherein the aryl and heteroaryl radicals are optionally substituted at a substitutable position with one or more radicals selected from halo, alkylthio, alkylsulfinyl, alkyl, cyano, haloalkyl, hydroxyl, alkoxy, hydroxyalkyl and haloalkoxy;

wherein $R^2$ is selected from heteroaryl and aryl, wherein the heteroaryl and aryl radicals are optionally substituted with one or more radicals selected from halo, alkylthio, alkylsulfinyl, alkyl, cyano, carboxyl, alkoxycarbonyl, haloalkyl, hydroxyl, alkoxy, hydroxyalkyl, alkoxyalkyl, haloalkoxy, amino, alkylamino, arylamino and nitro; and wherein $R^3$ is selected from alkyl, haloalkyl and amino;

provided $R^1$ is not haloalkyl substituted hydroxyalkyl, haloalkyl substituted aminoalkyl, haloalkyl substituted acylalkoxy, trifluoracetyl or urea substituted alkylthio when $R^3$ is methyl; further provided $R^1$ is not alkyl when $R^3$ is methyl and $R^2$ is phenyl optionally substituted with methyl, methoxy or chloro; and further provided $R^1$ is not halo when $R^3$ is methyl and $R^2$ is pyridyl or optionally substituted phenyl;

or a pharmaceutically-acceptable salt thereof.

The phrase "further provided", as used in the above description, is intended to mean that the denoted proviso is not to be considered conjunctive with any of the other provisos.

Compounds of Formula I would be useful for, but not limited to, the treatment of inflammation in a subject, and for treatment of other inflammation-associated disorders, such as, as an analgesic in the treatment of pain and headaches, or as an antipyretic for the treatment of fever. For example, compounds of Formula I would be useful to treat arthritis, including but not limited to rheumatoid arthritis, spondyloarthopathies, gouty arthritis, osteoarthritis, systemic lupus erythematosus and juvenile arthritis. Such compounds of Formula I would be useful in the treatment of asthma, bronchitis, menstrual cramps, tendinitis, bursitis, and skin related conditions such as psoriasis, eczema, burns and dermatitis. Compounds of Formula I also would be useful to treat gastrointestinal conditions such as inflammatory bowel disease, Crohn's disease, gastritis, irritable bowel syndrome and ulcerative colitis and for the prevention of colorectal cancer. Compounds of Formula I would be useful in treating inflammation in such diseases as vascular diseases, migraine headaches, periarteritis nodosa, thyroiditis, aplastic anemia, Hodgkin's disease, sclerodoma, rheumatic fever, type I diabetes, myasthenia gravis, sarcoidosis, nephrotic syndrome, Behcet's syndrome, polymyositis, gingivitis, hypersensitivity, conjunctivitis, swelling occurring after injury, myocardial ischemia, and the like. The compounds are useful as antiinflammatory agents, such as for the treatment of arthritis, with the additional benefit of having significantly less harmful side effects.

As, illustrated, the imidazoles of Formula I and I' are magnetically and structurally equivalent because of the prototropic tautomeric nature of the acidic hydrogen [A. R. Katritzky and C. W. Rees, "*Imidazoles and their Benzo Derivatives*" Comprehensive Heterocyclic Chemistry, Vol. 5, 363–365 (1984)]:

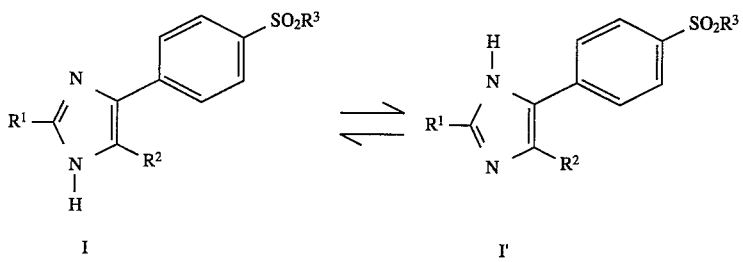

The present invention preferably includes compounds which selectively inhibit cyclooxygenase II over cyclooxygenase I. Preferably, the compounds have a cyclooxygenase II $IC_{50}$ of less than about 0.2 μM, and also have a selectivity ratio of cyclooxygenase II inhibition over cyclooxygenase I inhibition of at least 50, and more preferably of at least 100. Even more preferably, the compounds have a cyclooxygenase I $IC_{50}$ of greater than about 1 μM, and more preferably of greater than 10 μM. Such preferred selectivity may indicate an ability to reduce the incidence of common NSAID-induced side effects.

A preferred class of compounds consists of those compounds of Formula I wherein $R^1$ is selected from lower alkyl, lower haloalkyl, lower aralkyl, lower heterocyclicalkyl, lower heteroaralkyl, acyl, cyano, lower alkoxy, lower alkylthio, lower alkylthioalkyl, lower alkylsulfonyl, lower haloalkylsulfonyl, lower arylsulfonyl, halo, lower hydroxyalkyl, lower alkoxyalkyl, lower alkylcarbonyl, lower arylcarbonyl, lower aralkylcarbonyl, lower cyanoalkyl, lower aralkenyl, lower aminoalkyl, lower alkylaminoalkyl, lower N-arylaminoalkyl, lower N-alkyl-N-arylaminoalkyl, lower carboxyalkyl, lower alkoxycarbonylalkyl, lower alkoxycarbonyl, lower haloalkylcarbonyl, carboxyl, aminocarbonyl, lower alkylaminocarbonyl, lower alkylaminocarbonylalkyl, lower aralkoxy, lower aralkylthio, lower heteroaralkoxy, lower heteroaralkylthio, lower heteroarylalkoxyalkyl, lower heteroaryloxyalkyl, lower heteroarylthioalkyl, lower heteroarylalkylthioalkyl, heteroaryloxy, heteroarylthio, lower arylthioalkyl, lower aryloxyalkyl, lower haloaryloxyalkyl, arylthio, aryloxy, lower aralkylthioalkyl, lower aralkoxyalkyl, lower alkoxyaralkoxyalkyl, aryl and heteroaryl, wherein the aryl and heteroaryl radicals are optionally substituted at a substitutable position with one or more radicals selected from halo, lower alkylthio, lower alkylsulfinyl, lower alkyl, cyano, lower haloalkyl, lower hydroxyl, lower alkoxy, lower hydroxyalkyl and lower haloalkoxy;

wherein $R^2$ is selected from heteroaryl and aryl, wherein the heteroaryl and aryl radicals are optionally substituted with one or more radicals selected from halo, lower alkylthio, lower alkylsulfinyl, lower alkyl, cyano, carboxyl, lower alkoxycarbonyl, lower haloalkyl, hydroxyl, lower alkoxy, lower hydroxyalkyl, lower alkoxyalkyl, lower haloalkoxy, amino, lower alkylamino, arylamino and nitro; and wherein $R^3$ is selected from lower alkyl, lower haloalkyl and amino;

or a pharmaceutically-acceptable salt thereof.

A more preferred class of compounds consists of those compounds of Formula I wherein $R^1$ is selected from lower alkyl, lower haloalkyl, lower hydroxyalkyl, lower aralkenyl, lower aryloxyalkyl, lower arylthioalkyl and heteroaryl selected from 2-thienyl, 2-furyl, 3-furyl, 2-pyridyl, 4-pyridyl and 2-benzofuryl;

wherein $R^2$ is selected from heteroaryl and aryl, wherein the heteroaryl and aryl radicals are optionally substituted at a substitutable position with one or more radicals selected from halo, lower alkylthio, lower alkylsulfinyl, lower alkyl, cyano, carboxyl, lower alkoxycarbonyl, lower haloalkyl, hydroxyl, lower alkoxy, lower hydroxyalkyl, lower alkoxyalkyl, lower haloalkoxy, amino, lower alkylamino, phenylamino and nitro; and wherein $R^3$ is selected from lower alkyl and amino;

or a pharmaceutically-acceptable salt thereof.

A class of compounds of particular interest consists of those compounds of Formula I wherein $R^1$ is selected from methyl, ethyl, propyl, isopropyl, butyl, isobutyl, tert-butyl, pentyl, hexyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxymethyl, 2-phenylethenyl, phenoxymethyl, phenylthiomethyl, 3-furyl, 2-furyl, 2-benzofuryl; wherein $R^2$ is selected from phenyl, naphthyl and benzodioxolyl, wherein the phenyl, naphthyl and benzodioxolyl radicals are optionally substituted at a substitutable position with one or more radicals selected from fluoro, chloro, bromo, iodo, methyl, ethyl, isopropyl, tert-butyl, isobutyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methoxy, ethoxy, isopropoxy, tert-butoxy, propoxy, butoxy, isobutoxy, pentoxy, methylenedioxy, amino, trifluoromethoxy, cyano, carboxyl, methoxycarbonyl, ethoxycarbonyl, isopropoxycarbonyl, tert-butoxycarbonyl, propoxycarbonyl, butoxycarbonyl, isobutoxycarbonyl, pentoxycarbonyl, hydroxyl, nitro, methylsulfinyl, butylsulfinyl, hydroxymethyl, methoxymethyl, ethoxymethyl, methylamino, phenylamino, methylthio, ethylthio, propylthio and butylthio; or a pharmaceutically-acceptable salt thereof.

A family of specific compounds of particular interest within Formula I consists of compounds and pharmaceutically-acceptable salts thereof as follows:

5-(3-chlorophenyl)-4-(4-methylsulfonylphenyl)-2-trifluoromethyl-1H-imidazole;
5-(3-chloro-4-methylphenyl)-4-(4-methylsulfonylphenyl)-2-trifluoromethyl-1H-imidazole;
5-(3-fluorophenyl)-4-(4-methylsulfonylphenyl)-2-trifluoromethyl-1H-imidazole;
5-(5-chloro-4-methoxyphenyl)-4-(4-methylsulfonylphenyl)-2-trifluoromethyl-1H-imidazole;
5-(2,4-dichlorophenyl)-4-(4-methylsulfonylphenyl)-2-trifluoromethyl-1H-imidazole;
5-(4-bromophenyl)-4-(4-methylsulfonylphenyl)-2-trifluoromethyl-1H-imidazole;
4-(4-methylsulfonylphenyl)-2-trifluoromethyl-5-(4-trifluoromethylphenyl)-1H-imidazole;
4-(4-methylsulfonylphenyl)-2-trifluoromethyl-5-(4-trifluoromethoxyphenyl)-1H-imidazole;
5-(4-ethylphenyl)-4-(4-methylsulfonylphenyl)-2-trifluoromethyl-1H-imidazole;
5-(4-butylphenyl)-4-(4-methylsulfonylphenyl)-2-trifluoromethyl-1H-imidazole;
5-(4-butoxyphenyl)-4-(4-methylsulfonylphenyl)-2-trifluoromethyl-1H-imidazole;
4-(4-methylsulfonylphenyl)-5-(4-methylthiophenyl)-2-trifluoromethyl-1H-imidazole;
5-(3,5-dichloro-4-methoxyphenyl)-4-(4-methylsulfonylphenyl)-2-trifluoromethyl-1H-imidazole;
5-(3,5-dichloro-4-methylphenyl)-4-(4-methylsulfonylphenyl)-2-trifluoromethyl-1H-imidazole;
5-[4-(4-methylsulfonylphenyl)-2-trifluoromethyl-1H-imidazol-5-yl]-1,3-benzodioxole;
2-(4-chlorophenoxy)methyl-5-(4-chlorophenyl)-4-(4-methylsulfonylphenyl)-1H-imidazole;
5-(4-chlorophenyl)-2-[(4-fluorophenoxy)methyl]-4-(4-methylsulfonylphenyl)-1H-imidazole;
5-(4-chlorophenyl)-4-(4-methylsulfonylphenyl)-2-(phenylthiomethyl)-1H-imidazole;
5-(4-chlorophenyl)-2-[(4-methoxybenzyloxy)methyl]-4-(4-methylsulfonylphenyl)-1H-imidazole;
2-benzyl-5-(4-chlorophenyl)-4-(4-methylsulfonylphenyl)-1H-imidazole;
5-(4-chlorophenyl)-4-(4-methylsulfonylphenyl)-2-(phenylethyl)-1H-imidazole;
5-(4-chlorophenyl)-4-(4-methylsulfonylphenyl)-2-(phenylcarbonyl)-1H-imidazole;
5-(4-chlorophenyl)-4-(4-methylsulfonylphenyl)-2-phenoxymethyl-1H-imidazole;
5-(4-chlorophenyl)-4-(4-methylsulfonylphenyl)-2-(2-phenyl-trans-eth-1-ene)-1H-imidazole;
2-(2-benzofuryl)-5-(4-chlorophenyl)-4-(4-methylsulfonylphenyl)-1H-imidazole;
5-(4-chlorophenyl)-4-(4-methylsulfonylphenyl)-2-(2-furyl)-1H-imidazole;
2-benzylthio-5-(4-chlorophenyl)-4-[4-methylsulfonyl)phenyl]imidazole;
5-(4-chlorophenyl)-4-[4-(methylsulfonyl)phenyl]-2-(trifluoromethyl)-1H-imidazole;
5-(4-chlorophenyl)-2-(3-furyl)-4-[4-(methylsulfonyl)phenyl]-1H-imidazole;
4-(4-methylsulfonylphenyl)-5-phenyl-2-phenoxymethyl-1H-imidazole;
4-(4-methylsulfonylphenyl)-5-phenyl-2-(2-phenyl-trans-eth-1-ene)-1H-imidazole;
2-(2-benzofuryl)-4-(4-methylsulfonylphenyl)-5-phenyl-1H-imidazole;
2-(2-furyl)-4-(4-methylsulfonylphenyl)-5-phenyl-1H-imidazole;
2-benzylthio-4-[4-(methylsulfonyl)phenyl]-5-phenyl-imidazole;

4-[4-(methylsulfonyl)phenyl]-5-phenyl-2-trifluoromethyl)-1H-imidazole;

2-(3-furyl)-4-[4-(methylsulfonyl)phenyl]-5-phenyl-1H-imidazole;

4-[5-(3-chlorophenyl)-2-trifluoromethyl-1H-imidazol-4-yl]benzenesulfonamide;

4-[5-(3-chloro-4-methylphenyl)-2-trifluoromethyl-1H-imidazol-4-yl]benzenesulfonamide;

4-[5-(3-fluorophenyl)-2-trifluoromethyl-1H-imidazol-4-yl]benzenesulfonamide;

4-[5-(3-chloro-4-methoxyphenyl)-2-trifluoromethyl-1H-imidazol-4-yl]benzenesulfonamide;

4-[5-(2,4-dichlorophenyl)-2-trifluoromethyl-1H-imidazol-4-yl]benzenesulfonamide;

4-[5-(4-bromophenyl)-2-trifluoromethyl-1H-imidazol-4-yl]benzenesulfonamide;

4-[2-trifluoromethyl-5-(4-trifluoromethylphenyl)-1H-imidazol-4-yl]benzenesulfonamide;

4-[2-trifluoromethyl-5-(4-trifluoromethoxyphenyl)-1H-imidazol-4-yl]benzenesulfonamide;

4-[5-(4-ethylphenyl)-2-trifluoromethyl-1H-imidazol-4-yl]benzenesulfonamide;

4-[5-(4-butylphenyl)-2-trifluoromethyl-1H-imidazol-4-yl]benzenesulfonamide;

4-[5-(4-butoxyphenyl)-2-trifluoromethyl-1H-imidazol-4-yl]benzenesulfonamide;

4-[5-(4-methylthiophenyl)-2-trifluoromethyl-1H-imidazol-4-yl]benzenesulfonamide;

4-[5-(3,5-dichloro-4-methoxyphenyl)-2-trifluoromethyl-1H-imidazol-4-yl]benzenesulfonamide;

5-[(3,5-dichloro-4-methylphenyl)-2-trifluoromethyl-1H-imidazol-4-yl]benzenesulfonamide;

5-[4-(4-aminosulfonylphenyl)-2-trifluoromethyl-1H-imidazol-5-yl]-1,3-benzodioxole;

4-[2-(4-chlorophenoxy)methyl-5-(4-chlorophenyl)-1H-imidazol-4-yl]benzenesulfonamide;

4-[5-(4-chlorophenyl)-2-[(4-fluorophenoxy)methyl]-1H-imidazol-4-yl]benzenesulfonamide;

4-[5-(4-chlorophenyl)-2-(phenylthiomethyl)-1H-imidazol-4-yl]benzenesulfonamide;

4-[5-(4-chlorophenyl)-2-[(4-methoxybenzyloxy)methyl]-1H-imidazol-4-yl]benzenesulfonamide;

4-[2-benzyl-5-(4-chlorophenyl)-1H-imidazol-4-yl]benzenesulfonamide;

4-[5-(4-chlorophenyl)-2-(phenylethyl)-1H-imidazol-4-yl]benzenesulfonamide;

4-[5-(4-chlorophenyl)-2-(phenylcarbonyl)-1H-imidazol-4-yl]benzenesulfonamide;

4-[5-(4-chlorophenyl)-2-phenoxymethyl-1H-imidazol-4-yl]benzenesulfonamide;

4-[5-(4-chlorophenyl)-2-(2-phenyl-trans-eth-1-ene)-1H-imidazol-4-yl]benzenesulfonamide;

4-[2-(2-benzofuryl)-5-(4-chlorophenyl)-1H-imidazol-4-yl]benzenesulfonamide;

4-[5-(4-chlorophenyl)-2-(2-furyl)-1H-imidazol-4-yl]benzenesulfonamide;

4-[2-benzylthio-5-(4-chlorophenyl)-1H-imidazol-4-yl]benzenesulfonamide;

4-[5-(4-chlorophenyl)-2-(trifluoromethyl)-1H-imidazol-4-yl]benzenesulfonamide;

4-[5-(4-chlorophenyl)-2-(3-furyl)-1H-imidazol-4-yl]benzenesulfonamide;

4-[5-phenyl-2-phenoxymethyl-1H-imidazol-4-yl]benzenesulfonamide;

4-[5-phenyl-2-(2-phenyl-trans-eth-1-ene)-1H-imidazol-4-yl]benzenesulfonamide;

4-[2-(2-benzofuryl)-5-phenyl-1H-imidazol-4-yl]benzenesulfonamide;

4-[2-(2-furyl)-5-phenyl-1H-imidazol-4-yl]benzenesulfonamide;

4-[2-benzylthio-5-phenyl-imidazol-4-yl]benzenesulfonamide;

4-[5-phenyl-2-(trifluoromethyl)-1H-imidazol-4-yl]benzenesulfonamide;

4-[2-(3-furyl)-5-phenyl-1H-imidazol-4-yl]benzenesulfonamide;

5-(4-fluorophenyl)-4-(4-methylsulfonylphenyl)-2-trifluoromethyl-1H-imidazole;

5-(4-fluorophenyl)-4-(4-methylsulfonylphenyl)-2-phenoxymethyl-1H-imidazole;

5-(4-fluorophenyl)-4-(4-methylsulfonylphenyl)-2-(2-phenyl-trans-eth-1-ene)-1H-imidazole;

2-(2-benzofuryl)-5-(4-fluorophenyl)-4-(4-methylsulfonylphenyl)-1H-imidazole;

5-(4-fluorophenyl)-2-(2-furyl)-4-(4-methylsulfonylphenyl)-1H-imidazole;

5-(4-fluorophenyl)-2-methyl-4-(4-methylsulfonylphenyl)-1H-imidazole;

5-4-fluorophenyl)-2-isopropyl-4-(4-methylsulfonylphenyl)-1H-imidazole;

5-4-fluorophenyl)-2-hydroxymethyl-4-(4-methylsulfonylphenyl)-1H-imidazole;

2-benzylthio-5-(4-fluorophenyl)-4-[4-(methylsulfonyl)phenyl]imidazole;

5-(3-fluoro-4-methoxyphenyl)-4-[4-(methylsulfonyl)phenyl]-2-(trifluoromethyl)-1H-imidazole;

5-(4-chlorophenyl)-4-[4-(methylsulfonyl)phenyl]-2-(trifluoromethyl)-1H-imidazole;

5-(2-chlorophenyl)-4-[4-(methylsulfonyl)phenyl]-2-(trifluoromethyl)-1H-imidazole;

5-(3,4-dichlorophenyl)-4-[4-(methylsulfonyl)phenyl]-2-(trifluoromethyl)-1H-imidazole;

4-[4-(methylsulfonyl)phenyl]-5-(2-naphthyl)-2-(trifluoromethyl)-1H-imidazole;

5-(4-methoxyphenyl)-4-[4-(methylsulfonyl)phenyl]-2-(trifluoromethyl)-1H-imidazole;

5-(4-methylphenyl)-4-[4-(methylsulfonyl)phenyl]-2-(trifluoromethyl)-1H-imidazole;

5-(2,4-difluorophenyl)-4-[4-(methylsulfonyl)phenyl]-2-(trifluoromethyl)-1H-imidazole;

5-(3,4-difluorophenyl)-4-[4-(methylsulfonyl)phenyl]-2-(trifluoromethyl)-1H-imidazole;

4-[4-(methylsulfonyl)phenyl]-5-phenyl-2-(trifluoromethyl)-1H-imidazole;

5-(4-fluorophenyl)-2-(3-furyl)-4-(4-methylsulfonylphenyl)-1H-imidazole;

4-[5-(4-fluorophenyl)-2-(trifluoromethyl)-1H-imidazol-4-yl]benzenesulfonamide;

4-[5-(4-fluorophenyl)-2-phenoxymethyl-1H-imidazol-4-yl]benzenesulfonamide;

4-[5-(4-fluorophenyl)-2-(2-phenyl-trans-eth-1-ene)-1H-imidazol-4-yl]benzenesulfonamide;

4-[5-(4-fluorophenyl)-2-(2-benzofuryl)-1H-imidazol-4-yl]benzenesulfonamide;

4-[5-(4-fluorophenyl)-2-isopropyl-1H-imidazol-4-yl]benzenesulfonamide;

4-[5-(4-fluorophenyl)-2-methyl-1H-imidazol-4-yl]benzenesulfonamide;

4-[5-(4-fluorophenyl)-2-(2-furyl)-1H-imidazol-4-yl]benzenesulfonamide;

4-[2-benzylthio-5-(4-fluorophenyl)-1H-imidazol-4-yl]benzenesulfonamide;

4-[5-(4-fluorophenyl)-2-hydroxymethyl-1H-imidazol-4-yl]benzenesulfonamide;

4-[5-(3-fluoro-4-methoxyphenyl)-2-(trifluoromethyl)-1H-imidazol-4-yl]benzenesulfonamide;

4-[5-(4-chlorophenyl)-2-(trifluoromethyl)-1H-imidazol-4-yl]benzenesulfonamide;
4-[5-(2-chlorophenyl)-2-(trifluoromethyl)-1H-imidazol-4-yl]benzenesulfonamide;
4-[5-(3,4-dichlorophenyl)-2-(trifluoromethyl)-1H-imidazol-4-yl]benzenesulfonamide;
4-[5-(2-naphthyl)-2-(trifluoromethyl)-1H-imidazol-4-yl] benzenesulfonamide;
4-[5-(4-methoxyphenyl)-2-(trifluoromethyl)-1H-imidazol-4-yl]benzenesulfonamide;
4-[5-(4-methylphenyl)-2-(trifluoromethyl)-1H-imidazol-4-yl]benzenesulfonamide;
4-[5-(2,4-difluorophenyl)-2-(trifluoromethyl)-1H-imidazol-4-yl]benzenesulfonamide;
4-[5-(3,4-difluorophenyl)-2-(trifluoromethyl)-1H-imidazol-4-yl]benzenesulfonamide;
4-[5-phenyl-2-(trifluoromethyl)-1H-imidazol-4-yl]benzenesulfonamide; and
4-[5-(4-fluorophenyl)-2-(3-furyl)-1H-imidazol-4-yl]benzenesulfonamide.

Within Formula I there is a subclass of compounds of high interest represented by Formula II:

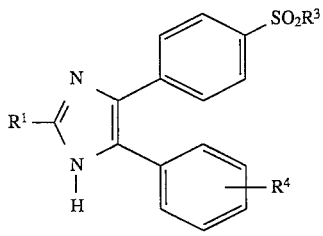

wherein $R^1$ is selected from lower alkyl, lower haloalkyl, lower hydroxyalkyl, lower aralkenyl, lower aryloxyalkyl, lower arylthioalkyl and heteroaryl;

wherein $R^3$ is selected from lower alkyl and amino; and
wherein $R^4$ is one or more radicals selected from hydrido, halo, lower alkyl and lower alkoxy; or where $R^4$ together with the phenyl radical forms naphthyl or benzodioxolyl;

provided $R^1$ is not lower alkyl when $R^3$ is methyl and when $R^4$ is hydrido, methyl, methoxy or chloro;

or a pharmaceutically-acceptable salt thereof.

A class of compounds of particular interest consists of those compounds of Formula II wherein $R^1$ is selected from methyl, ethyl, propyl, isopropyl, butyl, isobutyl, tert-butyl, pentyl, hexyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxymethyl, 2-phenylethenyl, phenoxymethyl, phenylthiomethyl, 3-furyl, 2-furyl, 2-benzofuryl; wherein $R^3$ is methyl or amino; and wherein $R^4$ is one or more radicals selected from hydrido, fluoro, chloro, bromo, methyl, ethyl, propyl, isopropyl, butyl, isobutyl, tert-butyl, methoxy, ethoxy, propoxy and n-butoxy; or where $R^4$ together with the phenyl radical forms naphthyl or benzodioxolyl; or a pharmaceutically-acceptable salt thereof.

The term "hydrido" denotes a single hydrogen atom (H). This hydrido radical may be attached, for example, to an oxygen atom to form a hydroxyl radical or two hydrido radicals may be attached to a carbon atom to form a methylene (—CH$_2$—) radical. Where used, either alone or within other terms such as "haloalkyl", "alkylsulfonyl", "alkoxyalkyl" and "hydroxyalkyl", the term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about six carbon atoms. Examples of such radicals include methyl, ethyl, n-propyl, isopropyl, n-butyl, isobutyl, sec-butyl, tert-butyl, pentyl, iso-amyl, hexyl and the like. The term "halo" means halogens such as fluorine, chlorine, bromine or iodine. The term "haloalkyl" embraces radicals wherein any one or more of the alkyl carbon atoms is substituted with halo as defined above. Specifically embraced are monohaloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of the same halo atoms or a combination of different halo radicals. "Lower haloalkyl" embraces radicals having 1–6 carbon atoms. Examples of haloalkyl radicals include fluoromethyl, difluoromethyl, trifluoromethyl, chloromethyl, dichloromethyl, trichloromethyl, trichloromethyl, pentafluoroethyl, heptafluoropropyl, difluorochloromethyl, dichlorofluoromethyl, difluoroethyl, difluoropropyl, dichloroethyl and dichloropropyl. The term "hydroxyalkyl" embraces linear or branched alkyl radicals having one to about ten carbon atoms any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl. The terms "alkoxy" and "alkoxyalkyl" embrace linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. The term "alkoxyalkyl" also embraces alkyl radicals having two or more alkoxy radicals attracted to the alkyl radical, that is, to form monoalkoxyalkyl and dialkoxyalkyl radicals. More preferred alkoxyalkyl radicals are "lower alkoxyalkyl" radicals having one to six carbon atoms and one or two alkoxy radicals. Examples of such radicals include methoxymethyl, methoxyethyl, ethoxyethyl, methoxybutyl and methoxypropyl. The "alkoxy" or "alkoxyalkyl" radicals may be further substituted with one or more halo atoms, such as fluoro, chloro or bromo, to provide "haloalkoxy" or haloalkoxyalkyl radicals. More preferred haloalkoxy radicals are "lower haloalkoxy" radicals having one to six carbon atoms and one or more halo radicals. Examples of such radicals include fluoromethoxy, chloromethoxy, trifluoromethoxy, trifluoroethoxy, fluoroethoxy and fluoropropoxy. The term "cyanoalkyl" embraces radicals having a cyano or nitrile (—CN) radical attached to an alkyl radicals as described above. More preferred cyanoalkyl radicals are "lower cyanoalkyl" radicals having one to six carbon atoms. Examples of such lower cyanoalkyl radicals include cyanomethyl, cyanopropyl, cyanoethyl and cyanobutyl. The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronaphthyl, indane and biphenyl. The term "heterocyclic" embraces saturated, partially saturated and unsaturated heteroatom-containing ring-shaped radicals, where the heteroatoms may be selected from nitrogen, sulfur and oxygen. Examples of saturated heterocyclic radicals include saturated 3 to 6-membered heteromonocylic group containing 1 to 4 nitrogen atoms [e.g. pyrrolidinyl, imidazolidinyl, piperidino, piperazinyl, etc.]; saturated 3 to 6-membered heteromonocyclic group containing 1 to 2 oxygen atoms and 1 to 3 nitrogen atoms [e.g. morpholinyl, etc.]; saturated 3 to 6-membered heteromonocyclic group containing 1 to 2 sulfur atoms and 1 to 3 nitrogen atoms [e.g., thiazolidinyl, etc.]. Examples of partially saturated heterocyclic radicals include dihydrothiophene, dihydropyran, dihydrofuran and dihydrothiazole. The term "heteroaryl" embraces unsaturated heterocyclic radicals. Examples of unsaturated heterocyclic radicals, also termed "heteroaryl" radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl [e.g., 4H-1,2,4-triazolyl, 1H-1,2,3-triazolyl, 2H-1,2,3-triazolyl, etc.] tetrazolyl [e.g. 1H-tetrazolyl, 2H-tetrazolyl, etc.], etc.; unsaturated condensed heterocyclic group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo [1,5-b]pyridazinyl, etc.], etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl, etc.] etc.; unsaturated condensed heterocyclic group containing 1 to 2 oxygen atoms and 1 to 3 nitrogen atoms [e.g. benzoxazolyl, benzoxadiazolyl, etc.]; unsaturated 3 to 6-membered heteromonocyclic group containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl, etc.] etc.; unsaturated condensed heterocyclic group containing 1 to 2 sulfur atoms and 1 to 3 nitrogen atoms [e.g., benzothiazolyl, benzothiadiazolyl, etc.] and the like. The term also embraces radicals where heterocyclic radicals are fused with aryl radicals. Examples of such fused bicyclic radicals include benzofuryl, benzothienyl, and the like. Said "heterocyclic" radicals may have 1 to 3 substituents such as lower alkyl, hydroxy, oxo, amino and lower alkylamino. More preferred heteroaryl radicals include five to six membered heteroaryl radicals. The term "heterocyclicalkyl" embraces heterocyclic-substituted alkyl radicals. More preferred heterocyclicalkyl radicals are "lower heterocyclicalkyl" radicals having one to six carbon atoms and a heterocyclic radical. Examples include such radicals as pyrrolidinylmethyl. The term "heteroarylalkyl" embraces heteroaryl-substituted alkyl radicals. More preferred heteroarylalkyl radicals are "lower heteroarylalkyl" radicals having one to six carbon atoms and a heteroaryl radical. Examples include such heteroarylalkyl radicals such as pyridylmethyl and thienylmethyl. The term "alkylthio" embraces radicals containing a linear or branched alkyl radical, of one to about ten carbon atoms attached to a divalent sulfur atom. More preferred alkylthio radicals are "lower alkylthio" radicals having alkyl radicals of one to six carbon atoms. Examples of such lower alkylthio radicals are methylthio, ethylthio, propylthio, butylthio and hexylthio. The term "alkylthioalkyl" embraces alkylthio radicals attached to an alkyl radical. More preferred alkylthioalkyl radicals are "lower alkylthioalkyl" radicals having alkyl radicals of one to six carbon atoms and an alkylthio radical as described above. Examples of such radicals include methylthiomethyl. The term "arylthio" embraces radicals containing an aryl radical, attached to a divalent sulfur atom, such as a phenylthio radical. The term "arylthioalkyl" embraces arylthio radicals attached to an alkyl radical. More preferred arylthioalkyl radicals are "lower arylthioalkyl" radicals having alkyl radicals of one to six carbon atoms and an arylthio radical as described above. Examples of such radicals include phenylthiomethyl. The term "alkylsulfinyl" embraces radicals containing a linear or branched alkyl radical, of one to ten carbon atoms, attached to a divalent —S(=O)— radical. More preferred alkylsulfinyl radicals are "lower alkylsulfinyl" radicals having one to six carbon atoms. Examples of such lower alkylsulfinyl radicals include methylsulfinyl, ethylsulfinyl, butylsulfinyl and hexylsulfinyl. The term "sulfonyl", whether used alone or linked to other terms such as alkylsulfonyl, denotes respectively divalent radicals —$SO_2$—. "Alkylsulfonyl" embraces alkyl radicals attached no a sulfonyl radical, where alkyl is defined as above. More preferred alkylsulfonyl radicals are "lower alkylsulfonyl" radicals having one to six carbon atoms. Examples of such lower alkylsulfonyl radicals include methylsulfonyl, ethylsulfonyl and propylsulfonyl. The "alkylsulfonyl" radicals may be further substituted with one or more halo atoms, such as fluoro, chloro or bromo, to provide "haloalkylsulfonyl" radicals. More preferred haloalkylsulfonyl radicals are "lower haloalkylsulfonyl" radicals having one or more halo atoms attached to lower alkylsulfonyl radicals as described above. Examples of such lower haloalkylsulfonyl radicals include fluoromethylsulfonyl, trifluoromethylsulfonyl and chloromethylsulfonyl. The term "arylsulfonyl" embraces aryl radicals as defined above, attached to a sulfonyl radical. Examples of such radicals include phenylsulfonyl. The terms "sulfamyl", "aminosulfonyl" and "sulfonamidyl" denotes $NH_2O_2S$—. The term "acyl" denotes a radical provided by the residue after removal of hydroxyl from an organic acid. Examples of such acyl radicals include formyl, alkanoyl and aroyl radicals. The terms "carboxy" or "carboxyl", whether used alone or with other terms, such as "carboxyalkyl", denotes —$CO_2H$. The term "carbonyl", whether used alone or with other terms, such as "alkoxycarbonyl", denotes —(C=O)—. The term "alkoxycarbonyl" means a radical containing an alkoxy radical, as defined above, attached via an oxygen atom to a carbonyl radical. Preferably, "lower alkoxycarbonyl" embraces alkoxy radicals having one to six carbon atoms. Examples of such "lower alkoxycarbonyl" ester radicals include substituted or unsubstituted methoxycarbonyl, ethoxycarbonyl, propoxycarbonyl, butoxycarbonyl and hexyloxycarbonyl. The term "aralkyl" embraces aryl-substituted alkyl radicals. Preferable aralkyl radicals are "lower aralkyl" radicals having aryl radicals attached to alkyl radicals having one to six carbon atoms. Examples of such radicals include benzyl, diphenylmethyl, triphenylmethyl, phenylethyl and diphenylethyl. The aryl in said aralkyl may be additionally substituted with halo, alkyl, alkoxy, haloalkyl and haloalkoxy. The terms benzyl and phenylmethyl are interchangeable. The term "aralkenyl" embraces aryl-substituted alkenyl radicals. Preferable aralkenyl radicals are "lower aralkenyl" radicals having aryl radicals attached to alkenyl radicals having two to six carbon atoms. Examples of such radicals include phenylethenyl and diphenylethenyl. The aryl in said aralkenyl may be additionally substituted with halo, alkyl, alkoxy, haloalkyl and haloalkoxy. The terms "alkylcarbonyl", "arylcarbonyl" and "aralkylcarbonyl" include radicals having alkyl, aryl and aralkyl radicals, respectively, as defined above, attached via an oxygen atom to a carbonyl radical. More preferred alkylcarbonyl radicals are "lower alkylcarbonyl" radicals having one to six carbon atoms. Examples of such radicals include methylcarbonyl and ethylcarbonyl. More preferred aralkylcarbonyl radicals are "lower aralkylcarbonyl" radicals having aryl radicals attached to alkyl radicals having one to six carbon atoms. Examples of such aralkylcarbonyl radicals include benzylcarbonyl. An example of an arylcarbonyl radical is phenylcarbonyl. The term "alkoxycarbonylalkyl" embraces radicals having "alkoxycarbonyl", as defined above substituted to an alkyl radical. More preferred alkoxycarbonylalkyl radicals are "lower alkoxycarbonylalkyl" having lower alkoxycarbonyl radicals as defined above attached to one to six carbon atoms. Examples of such lower alkoxycarbonylalkyl radicals include methoxycarbonylmethyl. The term "haloalkylcarbonyl" embraces radicals having a haloalkyl radical as described above attached to a carbonyl radical. More preferred radicals are "lower haloalkylcarbonyl" radicals where lower haloalkyl radicals, as described above are attached to a carbonyl radical. The terms "alkanoyl" or "carboxyalkyl" embrace radicals having a carboxy radical as defined above, attached to an alkyl radical. The alkanoyl radicals may be substituted or unsubstituted, such as formyl, acetyl, propionyl, butyryl, isobutyryl, valeryl, isovaleryl, pivaloyl, hexanoyl, trifluoroacetyl or the like, in which the preferable one is formyl, acetyl, propionyl or trifluoroacetyl. The term "heteroaralkyl" embraces heteroaryl-substituted alkyl radicals. More preferred heteroaralkyl radicals are "lower heteroaralkyl" radicals having five to six membered heteroaryl radicals attached to one to six carbon atoms. Examples of such radicals include pyridylmethyl, quinolylmethyl, thienylmethyl, furylethyl and quinolylethyl. The heteroaryl in said heteroaralkyl may be additionally substituted with halo, alkyl, alkoxy, haloalkyl and haloalkoxy. The term "aryloxy" embraces aryl radicals, as defined above, attached to an oxygen atom. The aryl in said aryloxy may be additionally substituted with one or more halo, alkyl, alkoxy, haloalkyl and haloalkoxy radicals. Examples of such radicals include phenoxy. The term "heteroaryloxy" embraces heteroaryl radicals as defined above attached to an oxygen radical. More preferred heteroaryloxy radicals are "lower heteroaryloxy" radicals having five to six membered heteroaryl radicals. The term "aralkoxy" embraces oxy-containing aralkyl radicals attached through an oxygen atom to other radicals. The term "aralkoxyalkyl" embraces alkyl radicals having one or more aralkoxy radicals attached to the alkyl radical, that is, to form monoaralkyloxyalkyl and diaralkyloxyalkyl radicals. The "aralkoxy" or "aralkoxyalkyl" radicals may be further substituted on the aryl ring portion of the radical. More preferred aralkoxyalkyl radicals are "lower aralkoxyalkyl" having an alkoxy attached to one to six carbon atoms. Examples of lower aralkoxyalkyl radicals include benzyloxymethyl. The term "heteroarylthio" embraces radicals having heteroaryl radicals attached to a sulfur radical. More preferred heteroarylthio radicals are "lower heteroarylthio" radicals having five to six membered heteroaryl radicals. Examples of such radicals include 2-furylthio, 2-thienylthio, 3-thienylthio, 4-pyridylthio and 3-pyridylthio. The term "alkoxyaralkoxyalkyl" embraces alkoxy substituted aralkoxyalkyl radicals. More preferred radicals have lower alkoxy substituted aralkoxyalkyl, where lower alkoxy is defined above. The terms "heteroaralkylthio" and "heteroaralkylthio" denote radicals having an heteroaryl radical attached to an alkylthio radical. More preferred heteroaralkylthio radicals are "lower heteroaralkylthio" radicals having heteroaryl radicals attached to lower alkylthio radicals as described above. Examples of such radicals include furylmethylthiomethyl and quinolylmethylthioethyl. The term "heteroarylalkylthioalkyl" denotes radicals having an heteroaryl radical attached to an alkylthio radical further attached through the sulfur atom to an alkyl radical. More preferred heteroarylalkylthioalkyl are "lower heteroarylalkylthioalkyl" radicals having lower heteroarylalkyl radicals as described above. Examples of such radicals include furylmethylthiomethyl and quinolylmethylthioethyl. The term "heteroarylthioalkyl" denotes radicals having an heteroaryl radical attached to a sulfur atom further attached through the sulfur atom to an alkyl radical. More preferred heteroarylthioalkyl radicals are "lower heteroarylthioalkyl" having lower heteroarylthio radicals as described above. Examples of such radicals include thienylthiomethyl and pyridylthiohexyl. The term "aralkylthio" embraces radicals having aralkyl radicals attached to a bridging sulfur atom. More preferred aralkylthio radicals are "lower aralkylthio" radicals having the aryl radicals attached to one to six carbon atoms. Examples of such radicals include benzylthio and phenylethylthio. The term "aralkylthioalkyl" embraces radicals having aralkyl radicals attached to alkyl radicals through a bridging sulfur atom. More preferred aralkylthioalkyl radicals are "lower aralkylthioalkyl" radicals having the aralkylthio radicals attached to one to six carbon atoms. Examples of such radicals include benzylthiomethyl and phenylethylthiomethyl. The term "heteroaryloxyalkyl" denotes radicals having an heteroaryl radical attached to an oxygen atom further attached through the oxygen atom to an alkyl radical. More preferred heteroaryloxyalkyl radicals are "lower heteroaryloxyalkyl" radicals having five to six membered heteroaryl radicals. Examples of such radicals include furylbutoxyethyl, pyridyloxymethyl and thienyloxyhexyl. The term "aminoalkyl" embraces alkyl radicals substituted with amino radicals. More preferred aminoalkyl radicals are "lower aminoalkyl" having one to six carbon atoms. Examples include aminomethyl, aminoethyl and aminobutyl. The term "alkylaminoalkyl" embraces aminoalkyl radicals having the nitrogen atom substituted with at least one alkyl radical. More preferred alkylaminoalkyl radicals are "lower alkylaminoalkyl" having one to six carbon atoms attached to a lower aminoalkyl radical as described above. More preferred alkylamino radicals are "lower alkylamino" radicals having one or two alkyl radicals of one to six carbon atoms, attached to a nitrogen atom. The term "alkylamino" denotes amino groups which have been substituted with one or two alkyl radicals. Suitable "alkylamino" may be mono or dialkylamino such as N-methylamino, N-ethylamino, N,N-dimethylamino, N,N-diethylamino or the like. The term "alkylaminocarbonyl" embraces alkylamino radicals, as described above, to a carbonyl radical. More preferred alkylaminocarbonyl radicals are "lower alkylaminocarbonyl" having lower alkylamino radicals, as described above, attached to a carbonyl radical. Examples of such radicals include N-methylaminocarbonyl and N,N-dimethylcarbonyl. The term "arylamino" denotes amino groups which have been substituted with one or two aryl radicals, such as N-phenylamino. The "arylamino" radicals may be further substituted on the aryl ring portion of the radical. The terms "N-arylaminoalkyl" and "N-aryl-N-alkyl-aminoalkyl" denote amino groups which have been substituted with one aryl radical or one aryl and one alkyl radical, respectively, and having the amino group attached to an alkyl radical. More preferred arylaminoalkyl radicals are "lower arylaminoalkyl" having the arylamino radical attached to one to six carbon atoms. Examples of such radicals include N-phenylaminomethyl and N-phenyl-N-methylaminomethyl. The term "aminocarbonyl" denotes an amide group of the formula —C(=O)NH$_2$. The term "alkylaminocarbonylalkyl" denotes an aminocarbonyl group which has been substituted with one or two alkyl radicals. More preferred are "lower alkylaminocarbonylalkyl" having lower alkylaminocarbonyl radicals as described above attached to one to six carbon atoms. The term "aryloxyalkyl" embraces alkyl radicals having one or more aryloxy radicals, aryl radicals attached to a divalent oxygen atom, attached to the alkyl radical, that is, to form monoaryloxyalkyl and diaryloxyalkyl radicals. The more preferred aryloxyalkyl radicals are "lower aryloxyalkyl" radicals having aryloxy radicals attached to one to six carbon atoms. Examples include phenoxymethyl. The terms "heteroaralkoxyalkyl" and "heteroarylalkoxyalkyl" embrace alkyl radicals having one or more heterocyclic radicals attached to an alkoxy radical, further attached to the alkyl radical. More preferred heteroaralkoxyalkyl radicals are "lower heteroaryl alkoxyalkyl" radicals having five to six membered heteroaryl radicals. Examples of such radicals include 2-thienylmethoxymethyl.

The present invention comprises a pharmaceutical composition comprising a therapeutically-effective amount of a compound of Formula I in association with at least one pharmaceutically-acceptable carrier, adjuvant or diluent.

The present invention also comprises a method of treating inflammation or inflammation-associated disorders in a subject, the method comprising administering to the subject having such inflammation or disorder a therapeutically-effective amount of a compound of Formula I.

Also included in the family of compounds of Formula I are the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicyclic, salicyclic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, stearic, cyclohexylaminosulfonic, algenic, β-hydroxybutyric, salicyclic, galactaric and galacturonic acid. Suitable pharmaceutically-acceptable base addition salts of compounds of Formula I include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of Formula I by reacting, for example, the appropriate acid or base with the compound of Formula I.

GENERAL SYNTHETIC PROCEDURES

The compounds of the invention can be synthesized according to the following procedures of Schemes I–IV, wherein the $R^1$–$R^4$ substituents are as defined for Formula I–II, above, except where further noted.

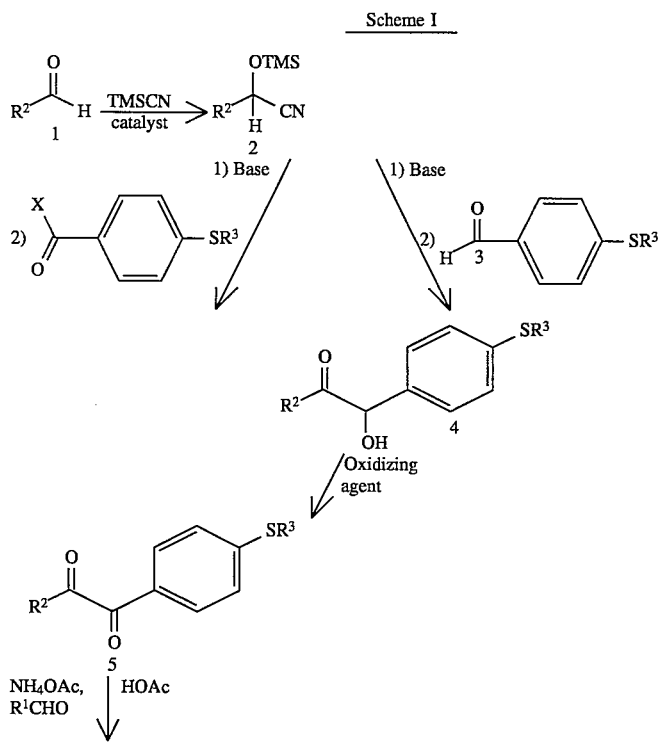

Scheme I

-continued
Scheme I

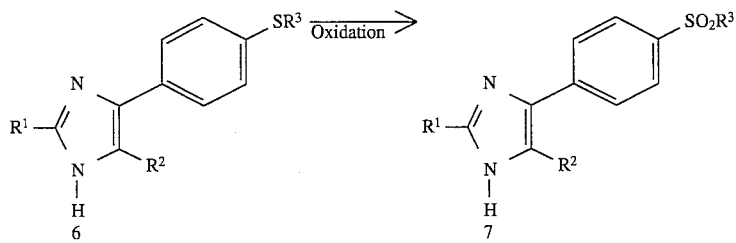

The subject imidazole compounds 7 of this invention may be synthesized according to the sequence outlined in Scheme I. Aldehyde 1 may be converted to the protected cyanohydrin 2 by reaction with a trialkylsilyl cyanide, such as trimethylsilyl cyanide (TMSCN) in the presence of a catalyst such as zinc iodide ($ZnI_2$) or potassium cyanide (KCN). Reaction of cyanohydrin 2 with a strong base followed by treatment with benzaldehyde 3 (where $R^5$ is alkyl) and using both acid and base treatments, in that order, on workup gives benzoin 4. Examples of strong bases suitable for this reaction are lithium diisopropylamide (LDA) and lithium hexamethyldisilazane. Benzoin 4 may be converted to benzil 5 by reaction with a suitable oxidizing agent, such as bismuth oxide or manganese dioxide, or by a Swern oxidation using dimethyl sulfoxide (DMSO) and trifluoroacetic anhydride. Benzil 5 may be obtained directly by reaction of the anion of cyanohydrin 2 with a substituted benzoic acid halide (where X is halo). Any of compounds 4 and 5 may be used as intermediates for conversion to imidazoles 6 (where $R^3$ is alkyl) according to chemical procedures known by those skilled in the art and described by M. R. Grimmett, "Advances in Imidazole Chemistry" in Advances in Heterocyclic Chemistry, 12, 104 (1970). The conversion of 5 to imidazoles 6 is carried out by reaction with ammonium acetate and an appropriate aldehyde (RlCHO) in acetic acid. Benzoin 4 may be converted to imidazoles 6 by reaction with formamide. In addition, benzoin 4 may be converted to imidazoles by first acylating with an appropriate acyl group ($R^1CO$—) and then treating with ammonium hydroxide. Those skilled in the art will recognize that the oxidation of the sulfide (where $R^3$ is methyl) to the methylsulfone (—$SO_2CH_3$) may be carried out at any point along the way beginning with compounds 4, and including oxidation of imidazoles 6, using, for examples, reagents such as hydrogen peroxide in acetic acid, m-chloroperoxybenzoic acid (MCPBA) and potassium peroxymonosulfate (OXONE®).

Scheme II

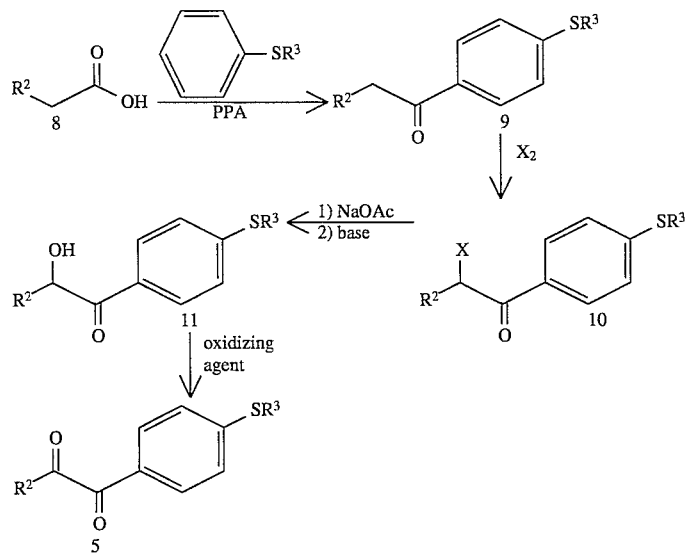

Alternative syntheses of benzoins and benzils may be carried out as described in Scheme II. Acylation of a thiobenzene derivative with an appropriately substituted acetic acid 8 using an acidic catalyst yields desoxybenzoin 9. Some suitable acidic catalysts include polyphosphoric acid (PPA), sulfuric acid, titanium tetrachloride, ferric chloride and stannic chloride. The resulting desoxybenzoin 9 may be halogenated to give haloketone 10 (where X is halo). Treatment of compound 10 with either water in a suitable co-solvent such as acetone, or with a carboxylate salt, followed by saponification with base, yields benzoin 11. Examples of bases suitable for saponification include sodium bicarbonate, sodium carbonate, potassium carbonate, sodium hydroxide and ammonium hydroxide. Examples of appropriate carboxylate salts include sodium acetate and sodium benzoate. Compound 11 is converted to benzil 5 by reaction with a suitable oxidizing agent such as bismuth oxide or manganese dioxide. Alternatively, benzil 5 may be synthesized directly from desoxybenzoin 9 by treatment with an appropriate oxidizing agent, such as selenious acid $H_2SeO_3$).

Haloketone 10 may be converted to imidazoles 6 by reaction either with formamide or with amidines.

Scheme III

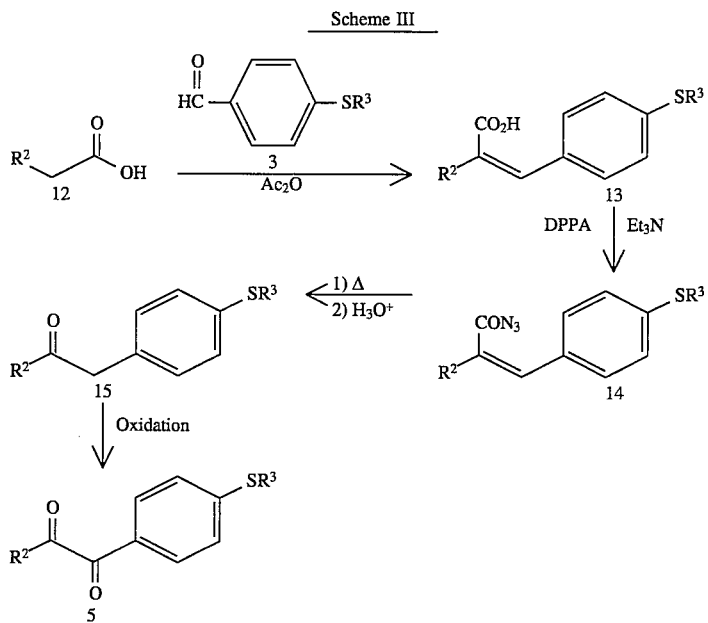

Scheme III outlines yet another method for the synthesis of benzil 5. Reaction of a suitable acetic acid derivative 12 with an aromatic aldehyde 3 in acetic anhydride yields unsaturated acid 13. Acid is converted to acyl azides 14 by reaction with diphenylphosphoryl azide (DPPA) in the presence of a base such as triethylamine ($Et_3N$) or by reaction of an activated carboxyl derivative of 13, such as an acid chloride or anhydride, with sodium azide. Decomposition of the acyl azide 14 by thermolysis, followed by hydrolysis with aqueous acid yields desoxybenzoin 15. Compound 15 may be converted to benzil 5 by oxidation according to procedures discussed in Schemes I–II.

Scheme IV

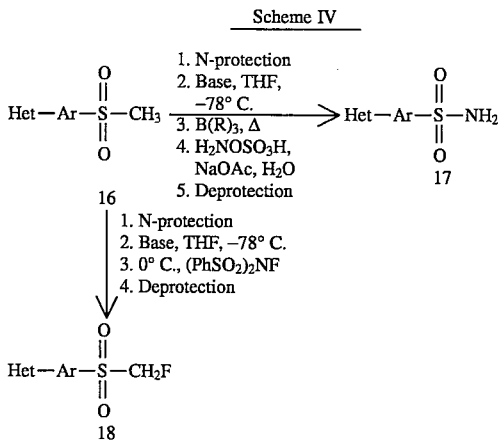

Synthetic Scheme IV shows the five step procedure used to prepare sulfonamide antiinflammatory agents 17 and the four step procedure used to prepare fluoromethylsulfone antiinflammatory agents 18 from their corresponding methyl sulfones 16. In step one, the imidazole 1H nitrogen of the imidazole ring of methyl sulfones 16 is protected with an appropriate protecting group, such as 2-(trimethylsilyl)ethoxymethyl chloride (SEM-Cl). In step two, THF solutions of the protected methyl sulfones 16 at –78° C. are treated with an alkyllithium reagent, e.g., methyllithium, n-butyllithium, or a Grignard reagent. In step three, the anions generated in step two are treated with an organoborane, e.g., triethylborane, tributylborane, etc., at –78° C. then allowed to warm to ambient temperature prior to stirring at reflux. In step four, an aqueous solution of sodium acetate and hydroxylamine-O-sulfonic acid is added to provide the corresponding protected sulfonamides. In step five, the amino protecting group is removed with mild acid to form the corresponding sulfonamide antiinflammatory agents 17 of this invention. Alternatively, the protected anion solutions generated in step two above may be warmed to 0° C. and treated with N-fluorodibenzenesulfonamide to provide the corresponding protected fluoromethylsulfones which can be deprotected with mild acid to form the corresponding antiinflammatory agents 18 of this invention.

The following examples contain detailed descriptions of the methods of preparation of compounds of Formula I–II. These detailed descriptions fall within the scope, and serve to exemplify, the above described General Synthetic Procedures which form part of the invention. These detailed descriptions are presented for illustrative purposes only and are not intended as a restriction on the scope of the invention. All parts are by weight and temperatures are in Degrees centigrade unless otherwise indicated. All compounds showed NMR spectra consistent with their assigned structures.

EXAMPLE 1

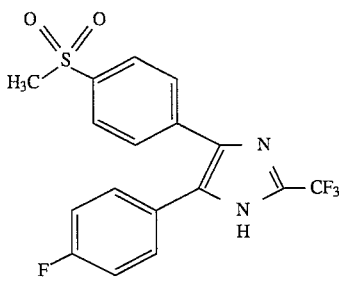

5-(4-Fluorophenyl)-4-(4-methylsulfonylphenyl)-2-trifluoromethyl-1H-imidazole

Method A
Step 1

Preparation of 4-Fluorophenyl-4'-methylthiophenyl-α-carboxystilbene (cis and trans)

4-Fluorophenylphenylacetic acid (23.5 g, 0.152 moles), p-methylthiobenzaldehyde (23.2 g, 0.152 moles), and triethylamine ($Et_3N$) (16.2 g, 0.16 moles) were dissolved in acetic anhydride (100 ml) and heated to reflux for 8 hours. After cooling, the contents were poured into water (500 ml) and stirred for 2 hours. The mixture was extracted with methylene chloride, dried ($MgSO_4$) and concentrated in vacuo. The residue was dissolved in methanol (300 ml), 2N KOH (potassium hydroxide) (100 ml) was added, and the contents were placed on a steam bath for 30 minutes. The mixture was cooled in ice and conc. HCl was added to reach pH 3, forming a precipitate. The precipitate was filtered, air dried and recrystallized from ethanol (EtOH) to give 24 g (50%) of 4-fluorophenyl-4'-methylthiophenyl-α-carboxystilbene (cis and trans) in the first crop: Anal. Calc'd. for $C_{16}H_{13}FO_2S$ (M.W.=288.34): C, 6.65; H, 4.54. Found: C, 66.71; H, 4.49.

Step 2

Preparation of 1-(4-Fluorophenyl)-2-(4-methylthiophenyl)-1-ethanone

A solution of the stilbene carboxylic acid (11.8 g, 41 mmol) from step 1, diphenylphosphoryl azide $(PhO)_2PON_3$ (12.5 g, 1.1 equiv.) and $Et_3N$ (5 g, 1.2 equiv.) in toluene (200 ml) was stirred for 1 hour at 25° C. The contents were poured into water (1 L), the layers separated and the organic layer was washed with brine. After filtration through $MgSO_4$, the toluene solution was heated at reflux for 1.5 hours under a nitrogen atmosphere. After cooling, the solvent was concentrated in vacuo, and the residue was heated to reflux with 2:1 acetic acid:water (50 ml) for 2 hours. After cooling, water (50 ml) was added and the precipitate was filtered, air dried and recrystallized from EtOH to give the ketone (7 g, 65%): m.p. 139°–140° C. Anal. Calc'd. for $C_{15}H_{13}FOS$ (M.W. 260.33): C, 69.21; H, 5.03; S, 12.32. Found: C, 68.94; H, 5.09; S, 12.15.

Step 3

Preparation of 1-(Fluorophenyl)-2-(4-methylsulfonylphenyl)-1-ethanone

A solution of 1-(4-fluorophenyl)-2-(4-methylthiophenyl)-1-ethanone from step 2 (15.7 g, 60 mmol) in methanol (500 ml) and tetrahydrofuran (200 ml) was stirred at 25° C. while a solution of OXONE® (40 g, excess) in water (150 ml) was added over 45 minutes. The entire reaction mixture was stirred at 40° C. for 3 hours. Water (500 ml) was added and the precipitate was filtered and air dried. The desired ketone was recrystallized by dissolving in warm chloroform and adding hexane until cloudy. The precipitate formed by cooling the solution in a refrigerator was filtered and air dried to give the titled ketone (15 g, 80%): m.p. 185°–187° C. Anal. Calc'd. for $C_{15}H_{13}FO_3S$ (M.W. 292.33): C, 61.63; H, 4.48; S, 10.97. Found: C, 61.72; H, 4.34; S, 11.01.

Step 4

Preparation of 1-(4-Methylsulfonylthenyl)-2-(4-fluorophenyl)-ethane-1,2-dione

A mixture of ketone from step 3 (1 g, 3.5 mmol), selenious acid ($H_2SeO_3$) (550 mg, 1.25 equiv.), dioxane (10 ml) and water (1 ml) were heated to reflux for 4 hours and cooled. The mixture was filtered and the filtrate evaporated. The residue was triturated with cold methanol and filtered to give 620 mg (60%) of the dione: m.p. 174°–175° C. Anal. Calc'd. for $C_{15}H_{11}FO_4S$ (M.W. 306.31): C, 58.82; H, 3.62; S, 10.47. Found: C, 58.70; H, 3.60; S, 10.70.

Step 5

Preparation of 5-(4-Fluorophenyl)-4-(4-methylsulfonylphenyl)-2-trifluoromethyl-1H-imidazole A mixture of dione from step 4 (1 g, 4.2 mmol), ammonium acetate (2.2 g, 5 equiv.), trifluoroacetaldehyde ethyl hemiacetal (2 g, 5 equiv.) and acetic acid (20 ml) was heated to reflux for 16 hours under an argon atmosphere. After cooling, the contents were poured into water (100 ml) and neutralized with ammonium hydroxide ($NH_4OH$) to pH 6.5. The precipitate was filtered, dried in an oven at 80° C. and recrystallized from ethyl acetate and hexane to give 5-(4-fluorophenyl)-4-(4-methylsulfonylphenyl)-2-trifluoromethyl-1H-imidazole (550 mg, 34%): m.p. 249°–250° C. (decomp.). Anal. Calc'd. for $C_{17}H_{12}F_4N_2O_2S$ (M.W. 384.35): C, 53.13; H, 3.15; N, 7.29; S, 8.34. Found: C, 52.91; H, 2.99; N, 6,97; S, 8.56.

Method B
Step 1

Preparation of 1-(4-Fluorophenyl)-2-(4-methylsulfonylphenyl)-2-bromoethane-1-one A suspension of 1-(4-fluorophenyl)-2-(methylsulfonylphenyl)-ethane-1-one (Method A, step 3) (24 g, 82 mmol) in acetic acid (500 ml) was warmed to 80° C. with stirring, and a solution of bromine (14.38 g, 0.09 moles) in acetic acid (50 ml) was added over 15 minutes. The reaction mixture became homogeneous, was cooled and stirred an additional 3 hours at 25°. The contents were poured into water (3 L) and extracted with ethyl acetate. The organic phase was washed with aqueous $NaHCO_3$, brine and dried ($MgSO_4$). The dried solution was concentrated in vacuo to give a solid which was triturated with cold ether to produce 26.5 g (87%) of the desired haloketone: m.p. 144°145° C. Anal. Calc'd. for $C_{15}H_{12}BrFO_3S$: C, 48.53; H, 3.26; Br, 21.52; S, 8.65. Found: C, 48.34; H, 3.28; Br, 21.19; S, 8.42.

Step 2

Preparation of 5-(4-Fluorophenyl)-4-(4-methylsulfonylphenyl)-2-trifluoromethyl-1H-imidazole A mixture of 1-(4-fluorophenyl)-2-(4-methylsulfonylphenyl)-2-bromo-ethane-1-one from step one (3 g, 8.2 mmol), trifluoroacetamidine (925 mg, 8.2 mmol), $NaHCO_3$ (690 mg, 8.2 mmol) and n-butanol (30 ml) was heated to reflux for 18 hours, cooled and concentrated. The residue was dissolved in water and methylene chloride, and the organic phase was separated, dried ($Na_2SO_4$) and concentrated. The residue was chromatographed on silica gel using methanol/toluene (5/95) and the crude product was recrystallized from ethyl acetate and hexane to give 700 mg (22%) of purified material which was identical to the material obtained in Method A, step 5.

Method C

Step 1

Preparation of 4-Fluoro-α-(trimethylsilyl)benzene-acetonitrile

To a solution of 50.0 g (403 mmoles) of 4-fluorobenzaldehyde in methylene chloride (100 mL) stirring in an ice bath under a nitrogen atmosphere, was added dropwise 54 ml (40 g, 403 moles) of trimethylsilyl cyanide. After the addition was complete, anhydrous zinc iodide (10 mg) was added, and stirring continued overnight while the mixture warmed to room temperature. The solvent was removed by distillation under reduced pressure, and continued distillation under high vacuum gave the title compound (82.2 g) as a very pale straw yellow liquid: b.p. 98°–100° C. at 0.8 mm Hg.

Step 2

Preparation of 1(4-Fluorophenyl)-2-(4-methylthiophenyl)-2-hydroxy-ethane-1-one To a cold (–70° C.) stirred solution of lithium bis(trimethylsilylamide) (11 ml of 1.0M in tetrahydrofuran, 11 mmol) in tetrahydrofuran (20 ml) under an argon atmosphere was added a solution of trimethylsilane (TMS) protected cyanohydrin of 4-fluorobenzaldehyde from step 1 (2.2 g, 0.01 mole) over 2 minutes and the reaction mixture was stirred cold (–70° C.) for 15 minutes. A mixture of 4-thiomethylbenzaldehyde (1.52 g, 0.01 moles) in tetrahydrofuran (10 ml) was added and the reaction mixture was warmed to –50° C. for 1 hour. Saturated ammonium chloride ($NH_4Cl$) (20 ml) was added and the mixture was warmed to 25° C. Water (20 ml) and methylene chloride ($CH_2Cl_2$) (25 ml) were added and the organic phase was separated and dried ($Na_2SO_4$). The organic solvent was evaporated and the residue was dissolved in methanol (10 ml) and treated with 5% $H_2SO_4$ (5 ml) at 25° C. overnight. Ether (25 ml) and water (50 ml) were added and the ether layer was separated. The ether layer was then stirred vigorously with 0.5N NaOH (30 ml) for 15 minutes. The ether layer was dried ($Na_2SO_4$), evaporated, and the residue chromatographed on silica gel with ethyl acetate/hexane (20/80) to yield 1.8 g (67%) of the titled ketone. Anal. Calc'd. for $C_{15}H_{13}FO_2S$ (M.W. 276.33): C, 65.20; H, 4.74; S, 11.60. Found: C, 65.10; H, 4.80; S, 11.75.

Step 3

Preparation of 1-(4-Methylthiophenyl)-2-(4-fluorophenyl)-ethane-1,2-dione

A mixture of ketone from step 2 (1.25 g, 4.5 mmol) and bismuth oxide ($Bi_2O_3$) (2.7 g, 1.2 equiv.) in acetic acid (20 ml) was warmed to 80° C. for 30 minutes. After cooling, the mixture was filtered through Celite® filter agent and the filtrate was concentrated. The residue was dissolved in hot methanol and filtered. The solvent was concentrated under a nitrogen stream, placed in the refrigerator and the precipitate formed was filtered to give 1 g (83%) of titled dione: m.p. 96°–97° C. Anal. Calc'd. for $C_{15}H_{11}FO_2S$ (M.W. 274.31): C, 65.68; H, 4.04; S, 11.69. Found: C, 65.42; H, 3.85; S, 1.42.

Step 4

Preparation of 5-(4-Fluorophenyl)-4-(4-methylthiophenyl)-2-trifluoromethyl-1H-imidazole Following the procedure of Example 1, Method A, step 5, and using the dione from step 3 above (1 g, 3.6 mmol), ammonium acetate (2.2 g, 5 equiv.), trifluoroacetaldehyde ethyl hemiacetal (1.25 g, 1.75 equiv.) and acetic acid (30 ml) gave a crude imidazole which was chromatographed on silica gel with toluene to afford 570 mg (45%) of the title compound.

Step 5

Preparation of 5-(4-Fluorophenyl)-4-(4-methylsulfonylphenyl)-2-trifluoromethyl-1H-imidazole A solution of imidazole from step 4 above (550 mg, 1.6 mmol) in methanol (10 ml) was stirred at 25° C. while a solution of OXONE® (1.6 g) in water (3 ml) was added. The reaction mixture was stirred for 3 hours at room temperature, poured into water (50 ml) and extracted with methylene chloride. After drying the organic layer ($Na_2SO_4$) and concentration, the residue was treated with cold ethyl acetate, filtered, and air dried to give 490 mg (80%) of the titled material which was identical with Examples 1 Method A and Method B.

EXAMPLE 2

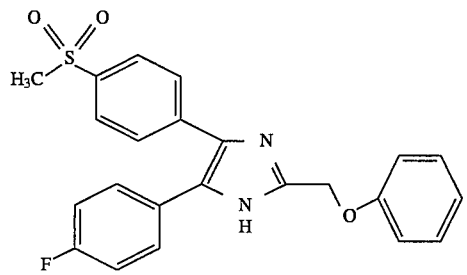

5-(4-Fluorophenyl)-4-(4-methylsulfonylphenyl)-2-phenoxymethyl-1H-imidazole

In a manner similar to Example 1, 1-(4-methylsulfonylphenyl)-2-(4-fluorophenyl)-ethane-1,2-dione (Example 1, Method A, step 4) (500 mg, 1.6 mmol), ammonium acetate (1.1 g, 5 equiv.), phenoxyacetaldehyde dimethyl acetal (800 mg, 2.5 equiv.) and acetic acid (20 ml) gave 4-(4-methylsulfonylphenyl)-5-(4-fluorophenyl)-2-phenoxymethyl-1H-imidazole (110 mg, 12%) after chromatography on silica gel using ethyl acetate/toluene (30/70) as the eluent and recrystallization from ethyl acetate and hexane: m.p. 189°–190° C. Anal. Calc'd. for $C_{23}H_{19}N_2O_3FS \cdot \frac{1}{4} H_2O$ (M.W. 426.98): C, 64.70; H, 4.60; N, 6.56; S, 7.51. Found: C, 64.62; H, 4.29; N, 6.22; S, 7.88.

EXAMPLE 3

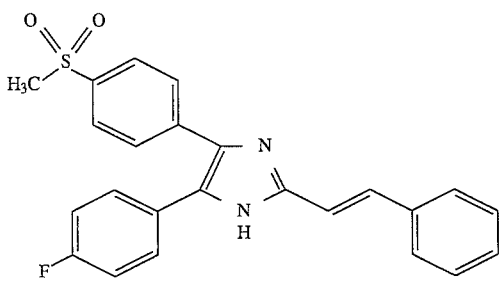

5-(4-Fluorophenyl)-4-(4-methylsulfonylphenyl)-2-(2-phenyl-trans-eth-1-ene)-1H-imidazole Following the procedure of Example 1, 1-(4-methylsulfonylphenyl)-2-(4-fluorophenyl)-ethane-1,2-dione (Example 1, Method A, step 4) (500 mg, 1.6 mmol), NH$_4$OAc (1.1 g, 14.3 mmol), trans-cinnamaldehyde (250 mg, 1.89 mmol) and acetic acid (20 ml) gave 121 mg (18%) of the desired imidazole after chromatography on silica gel with methanol: toluene (3:97) as the eluent and recrystallization from cyclohexane: m.p. 221°–224° C. Anal. Calc'd. for $C_{24}H_{19}N_2O_2FS$ (M.W. 418.49): C, 68.88; H, 4.58; N, 6.69; S, 7.66. Found: C, 68.44; H, 4,57; N, 6.45; S, 7.61.

EXAMPLE 4

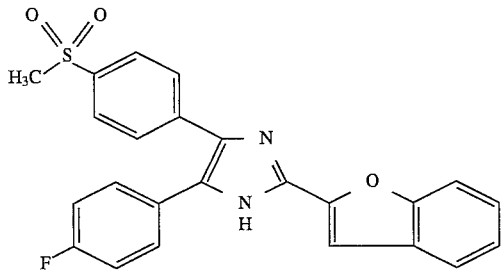

2-(2-Benzofuryl)-5-(4-fluorophenyl)-4-(4-methylsulfonylphenyl)-1H-imidazole

Following the procedure of Example 1, Method A, 1-(4-methylsulfonylphenyl)-2-(4-fluorophenyl)-ethane-1,2-dione (Example 1, Method A, step 4) (500 mg, 1.6 mmol), NH$_4$OAc (1.1 g, 14.3 mmol), benzofuran-2-carboxaldehyde (280 mg, 1.92 mmol) and acetic acid (20 ml) gave 2-(2-benzofuryl)-5-(4-fluorophenyl)-4-(4-methylsulfonylphenyl)-1H-imidazole (575 mg, 76%) after recrystallization from isopropanol and water: m.p. 235°–237° C. Anal. Calc'd. for $C_{24}H_{17}N_2O_3FS\cdot 2H_2O$ (M.W. 468.51): C, 61.53; H, 4.52; N, 5.98; S, 6.84. Found: C, 61.39; H, 4.27; N, 5.79; S, 6.82.

EXAMPLE 5

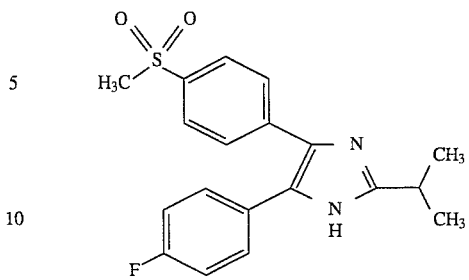

5-(4-Fluorophenyl)-2-isopropyl-4-(4-methylsulfonylphenyl)-1H-imidazole

Following the procedure of Example 1, Method A, 1-(4-methylsulfonylphenyl)-2-(4-fluorophenyl)-ethane-1,2-dione (Example 1, Method A, step 4) (500 mg, 1.6 mmol), ammonium acetate (1.1 g, 5 equiv.), isobutyraldehyde (140 mg, 1.25 equiv.) and acetic acid (20 ml) gave 4-(4-methylsulfonylphenyl)-5-(4-fluorophenyl)-2-isopropyl-1H-imidazole (380 mg, 66%) after recrystallization from ethyl acetate and hexane: m.p. 214°–215° C. Anal. Calc'd. for $C_{19}H_{19}N_2O_2FS$ (M.W. 358.44): C, 63.67; H, 5.34; N, 7.82; S, 8.95. Found: C, 63.49; H, 5.41; N, 7.62; S, 8.97.

EXAMPLE 6

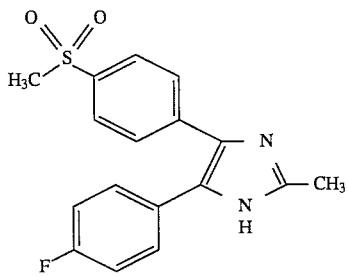

5-(4-Fluorophenyl)-2-methyl-4-(4-methylsulfonylphenyl)-1H-imidazole

Step 1 Preparation of 1-(4-methylthiophenyl)-2-(4-fluorophenyl)-1-ethanone

A mixture of polyphosphoric acid (160 g), 4-fluorophenylacetic acid (10 g, 65 mmol) and thioanisole (10 g, 1.2 equiv.) was heated and mechanically stirred to 125° C. for 20 minutes and cooled to 50° C. Ice was added rapidly with external cooling so as to maintain the internal temperature at about 50° C. After excess ice was added, the reaction was stirred for 30 minutes, filtered, and the filter cake air dried. The crude ketone was recrystallized from EtOH to give 10 g (60%) of ketone: Anal. Calc'd. for $C_{15}H_{13}FOS$ (M.W. 260.33): C, 69.21; H, 5.03; S, 12.32. Found: C, 69.14; H, 5.00; S, 12.23.

Step 2 Preparation of 1-(4-methylthiophenyl)-2-bromo-2-(4-fluorophenyl)-1-ethanone A mixture of 1-(4-methylthiophenyl)-2-(4-fluorophenyl)-1-ethanone from step 1 (9.48 g, 36 mmol) and acetic acid (200 ml) was stirred at 15° C. and a solution of bromine (5.80 g, 0.036 moles) in acetic acid (10 ml) was added dropwise over 5 minutes. The reaction mixture was stirred at 25° C. for an additional 2 hours. The mixture was poured into water (400 ml) with stirred for one hour. The precipitate formed was filtered, air dried and dried in vacuo at ambient temperature to give 11.4 g (93%) of the bromoketone: Anal. Calc'd. for $C_{15}H_{12}BrFOS$ (M.W. 339.23): C, 53.11; H, 3.57; S, 9.45; Br, 23.55. Found: C, 51.34; H, 3.34; S, 9.62; Br, 23.40.

Step 3 Preparation of 1-(4-methylthiophenyl)-2-(4-fluorophenyl)-1-ethanone-2-acetate A mixture of 1-(4-methylthiophenyl)-2-bromo-2-(4-fluorophenyl)-1-ethanone from step 2 (7.26 g, 21 mmol), sodium acetate (NaOAc) (8.6 g, 5 equiv.), dimethoxyethane (105 ml) and water (70 ml) was heated to reflux for 4 hours, cooled, poured into water (400 ml) and extracted with methylene chloride. The organic extract was dried (MgSO$_4$), filtered, concentrated in vacuo and the residue was chromatographed on silica gel with toluene to give 5 g (74%) of the acetate which slowly crystallized upon standing: Anal. Calc'd. for $C_{17}H_{15}FO_3S$ (M.W. 318.37): C, 64.14; H, 4.75; S, 10.07. Found: C, 63.89; H, 4.68; S, 9.81.

Step 4 Preparation of 4-(4-methylthiophenyl)-5-(4-fluorophenyl)-2-methyl-1H-imidazole The 1-(4-methylthiophenyl)-2-(4-fluorophenyl)-1-ethanone-2-acetate from step 3 (700 mg, 2.2 mmol) was heated to 180° C. in formamide (10 ml) under a nitrogen atmosphere for 2 hours. After cooling, the mixture was poured into water (50 ml) and extracted with methylene chloride. The extract was dried (Na$_2$SO$_4$), evaporated, and the residue chromatographed on silica gel with toluene/methanol (95/5) containing 0.5% NH$_4$OH to give 132 mg (20%) of imidazole: Anal. Calc'd. for $C_{17}H_{15}N_2FS$ (M.W. 298.38): C, 68.43; H, 5.07; N, 9.39; S, 10.17. Found: C, 68.14; H, 5.18; N, 9.09; S, 10.31.

Step 5 Preparation of 4-(4-methylsulfonylphenyl)-5-(4-fluorophenyl)-2-methyl-1H-imidazole In a manner similar to Example 1, Method C, step 4, 4-(4-methylthiophenyl)-5-(4-fluorophenyl)-2-methyl-1H-imidazole (114 mg, 0.4 mmol) from step 4 was converted to 5-(4-fluorophenyl)-2-methyl-4-(4-methylsulfonylphenyl)-1H-imidazole (107 mg, 95%): Anal. Calc'd. for $C_{17}H_{15}N_2O_2FS$ (M.W. 330.38): C, 61.80; H, 4.58; N, 8.48; S, 9.71. Found: C, 61.90; H, 4.61; N, 68.35; S, 9.39.

EXAMPLE 7

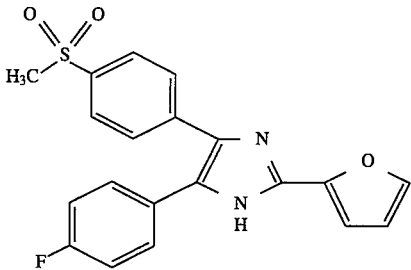

5-(4-Fluorophenyl)-2-(2-furyl)-4-(4-methylsulfonylphenyl)-1H-imidazole

In a manner similar to Example 1, Method A, 1-(4-methylsulfonylphenyl)-2-(4-fluorophenyl)-ethane-1,2-dione (Example 1, Method A, step 4) (500 mg, 1.6 mmol), ammonium acetate (1.1 g, 5 equiv.), 2-furaldehyde (170 mg, 1.1 equiv.) and acetic acid (20 ml) gave 308 mg (50%) of product after chromatography on silica gel with ethyl acetate/toluene (50/50) and recrystallization from isopropanol: m.p. 244°–246° C. (decomp.). Anal. Calc'd. for $C_{20}H_{15}N_2O_3FS$ (M.W. 382.42): C, 62.82; H, 3.95; N, 7.33; S, 8.38. Found: C, 62.63; H, 4.06; N, 7.13; S, 8.39.

EXAMPLE 8

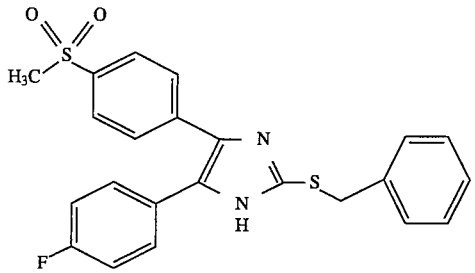

2-Benzylthio-5-(4-fluorophenyl)-4-[4-(methylsulfonyl)phenyl]-1H-imidazole

A mixture of S-benzylisothiourea hydrochloride (300 mg, 1.5 mmol), 1-(4-fluorophenyl)-2-(4-methylsulfonylphenyl)-2-bromoethan-1-one (Example 1, Method B, step 1) (500 mg, 1.3 mmol) and NaHCO$_3$ (500 mg, 6 mmol) in EtOH (10 ml) was heated to reflux for 3 hours. After evaporation of the solvent, the residue was treated with water (25 ml) and extracted with methylene chloride (25 ml). After drying (MgSO$_4$), the organic phase was evaporated. The residue was chromatographed on silica gel, eluting with ethyl acetate/toluene (25/75). The crude material was recrystallized from toluene and hexane to give 100 mg (17%) of titled product: m.p. 155°–156° C. Anal. Calc'd. for $C_{23}H_{19}FN_2O_2S_2$: C, 62.99; H, 4.37; N, 6.39; S, 14.62. Found: C, 62.93; H, 4.41; N, 5.98; S, 14.33.

EXAMPLE 9

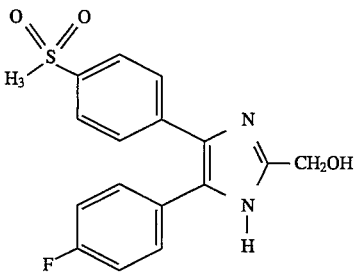

5-(4-Fluorophenyl)-2-hydroxymethyl-4-[4-(methylsulfonyl)phenyl]imidazole

Step 1 Preparation of 5-(4-fluorophenyl)-4-(4-methylthiophenyl)-1H-imidazole 1-(4-Fluorophenyl)-2-(4-methylthiophenyl)-2-hydroxyethane-1-one (Example 1, Method C, step 1) (12.25 g, 44 mmol) was heated at 200° C. in formamide (200 ml) for 4 hours under a nitrogen atmosphere. After cooling, the reaction was poured into 1 L of ice water and stirred rapidly for 30 minutes. The precipitate was filtered and air dried. The crude material was recrystallized from EtOH to give 7.5 g (60%) of imidazole: m.p. 195°–196° C. (decomp.). Anal. Calc'd. for $C_{16}H_{13}N_2FS$: C, 67.58; H, 4.61; N, 9.85; S, 11.28. Found: C, 67.51; H, 4.51; N, 9.68; S, 11.33.

Step 2 Preparation of 5-(4-fluorophenyl)-4-(4-methylthiophenyl)-1-(1-methyl-1-ethoxymethyl)-1H-imidazole A mixture of the imidazole described in step 1 (500 mg, 1.7 mmol), ethyl vinyl ether (250 mg, 3.4 mmol) and dichloroacetic acid (200 mg, 1.5 mmol) was heated to reflux in toluene (5 ml) for 6 hours. After cooling, the mixture was stirred with 1N NaOH (2 ml) for 30 minutes. The organic layer was separated and dried over K₂CO₃ (anhyd.) and the residue, after evaporation, was chromatographed on silica gel, eluting with toluene/methanol (95/5), to give 520 mg (86%) of the titled compound as an oil: Anal. Calc'd. for $C_{20}H_{21}N_2OFS$: C, 67.39; H, 5.94; N, 7.86; S, 8.99. Found: C, 67.51; H, 5.88; N, 7.55; S, 9.05.

Step 3 Preparation of 5-(4-fluorophenyl)-4-(4-methylthiophenyl)-1H-imidazole-2-carboxaldehyde A solution of the compound from step 2 (500 mg, 1.4 mmol) and tetramethylethylenediamine (TMEDA) (186 mg, 1.6 mmol) in tetrahydrofuran (8 ml) was cooled to −70° C. under an argon atmosphere. n-Butyllithium (1.2 ml of 1.6M solution in hexane, 1.9 mmol) was added and the solution stirred at −70° C. for 15 minutes. Dimethylformamide (DMF) (140 mg, 1.9 mmol) was added and the solution was warmed to 0° C. The reaction was quenched by the addition of saturated NaHCO₃ solution (2 ml) and extracted with diethyl ether. The organic phase was separated and dried (Na₂SO₄). The drying agent was filtered and the filtrate concentrated in vacuo. The residue was treated with 2N HCl (5 ml) in EtOH (10 ml) at room temperature for 24 hours. The reaction solution was made basic with NaHCO₃, diluted with water (20 ml) and extracted with methylene chloride. After evaporation, the residue was chromatographed on silica gel, eluting with toluene/methanol (90/10), to give 350 mg (70%) of titled compound which was used immediately without further purification.

Step 4 Preparation of 5-(4-fluorophenyl)-2-hydroxymethyl-4-(4-methylthiophenyl)-1H-imidazole A solution of compound from step 3 (350 mg, 1 mmol) and NaBH₄ (75 mg, 2 eg.) in methanol (10 ml) was stirred for 1 hour at 25° C. The reaction was acidified with 2N HCl (4 ml), stirred for 2 hours and placed on a steam bath for 2 minutes. After cooling, the mixture was neutralized with aqueous NaHCO₃ solution, extracted with methylene chloride, dried (MgSO₄) and evaporated. The residue was chromatographed on silica gel, eluting with toluene/methanol (90/10). The crude product was recrystallized from ethyl acetate/hexane to give 240 mg (78%) of pure 5-(4-fluorophenyl)-2-hydroxymethyl-4-(4-methylthiophenyl)-1H-imidazole: m.p. 108°–110° C. Anal. Calc'd. for $C_{17}H_{15}N_2OFS$: C, 64.95; H, 4.81; N, 8.91; S, 10.20. Found: C, 64.69; H, 4.92; N, 8.79; S, 10.41.

Step 5 Preparation of α-(4-fluorophenyl)-2-hydroxymethyl-4-[4-(methylsulfonyl)phenyl]imidazole A mixture of 2-hydroxymethyl-imidazole from step 4 (150 mg, 0.4 mmol), OXONE®(450 mg, excess), water (2 ml), methanol (5 ml) and tetrahydrofuran (3 ml) was stirred at 25° C. for 2 hours. The reaction mixture was diluted with water (20 ml) and extracted with methylene chloride. After removal of solvent, the crude material was recrystallized from toluene to give 80 mg (70%) of 4-(4-fluorophenyl)-2-hydroxymethyl-5-(4-methylsulfonylphenyl)- 1H-imidazole: m.p. 115°–117° C. Anal. Calc'd. for $C_{17}H_{18}N_2O_3FS·H_2O$: C, 56.03; 4.70; N, 7.69; S, 8.80. Found: C, 56.02; H, 4.64; N, 7.45; S, 8.90.

EXAMPLE 10

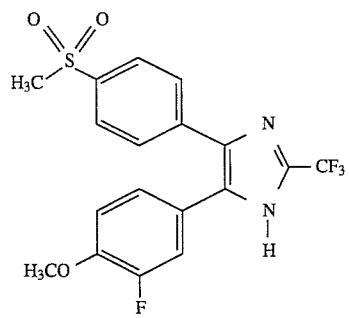

5-(3-Fluoro-4-methoxyphenyl)-4-[4-(methylsulfonyl)phenyl]-2-(trifluoromethyl)-1H-imidazole Step 1 Preparation of 3-fluoro-4-methoxy-α[(trimethylsilyl)oxy]benzeneacetonitrile 3-Fluoro-p-anisaldehyde (15 mmol, 2.31 g) and trimethylsilyl cyanide (16 mmol, 2.13 mL) were added to ZnI₂ (15 mg). The mixture was stirred for 3 hours at room temperature and vacuum distilled (ca. 1 torr, 105° C.) affording the title compound as an oil (3.38 g, 89%).

Step 2 Preparation of 1-(3-fluoro-4-methoxyphenyl)-2-hydroxy-2-[4-(methylthio)phenyl]ethanone A dry flask under an argon atmosphere containing tetrahydrofuran (25 mL) was cooled to −78° C. Lithium hexamethyldisilazide (1M in tetrahydrofuran, 15 mL) was introduced, followed by 3-fluoro-4-methoxy-α-[(trimethylsilyl)oxy]benzeneacetonitrile from step 1 (13. 4 mmol, 3.38 g), which was transferred using ca. 10 mL of tetrahydrofuran. After 20 minutes, (4-methylthio)benzaldehyde (14.4 mmol, 1.92 mL) was added. The reaction was quenched after an hour by addition of 5% HCl (60 mL) and KHF₂ (22 mmol, 1.75 g). The mixture was stirred for 1.5 hours at room temperature and extracted into ethyl acetate (150 mL). The organic phase was separated and stirred for 1 hour in the presence of aqueous NaOH (1.20 g in 50 mL). The organic layer was separated, dried over MgSO₄, concentrated in vacuo and subjected to chromatography, affording the title compound (2.00 g, 50%) as a waxy solid.

Step 3 Preparation of 1-(3-fluoro-4-methoxyphenyl)-2-[4-(methylthio)phenyl]ethane-1,2-dione 1-(3-Fluoro-4-methoxyphenyl)-2-hydroxy-2-[4-(methylthio)phenyl]ethanone from step 2 (6.5 mmol, 2.00 g) was diluted with glacial acetic acid (30 mL). Bismuth oxide (11.4 mmol, 5.30 g) was added and the mixture was heated at 90° C. for 2 hours. The crude mixture was filtered through Celite® filter agent, lyophilized and subjected to chromatography, affording the title compound as a yellow solid (642 mg, 32%).

Step 4 Preparation of 5-(3-fluoro-4-methoxyphenyl)-4-[4-(methylthio)phenyl]-2-(trifluoromethyl)-1H-imidazole To 1-(3-fluoro-4-methoxyphenyl)-2-[4-(methylthio)phenyl]ethane-1,2-dione from step 3 (2.1 mmol, 638 mg) was added ammonium acetate (12 mmol, 0.925 g), glacial acetic acid (10 mL) and trifluoroacetaldehyde ethyl hemiacetal (5.5 mmol, 0.64 mL). The mixture was brought to reflux. After 6 hours, additional hemiacetal (0.2 mL) was added and the mixture was heated an additional 16 hours. Lyophilization followed by chromatography (1:20 methanol in toluene) afforded the imidazole as a glass (526 mg).

Step 5 Preparation of 5-(3-fluoro-4-methoxyphenyl)-4-[4-(methylsulfonyl)phenyl]-2-(trifluoromethyl)-1H-imidazole 4-(3-Fluoro-4-methoxyphenyl)-5-[4-(methylthio)phenyl]-2-(trifluoromethyl)-1H-imidazole 516 mg, 1.35 mmol) from step 4 was dissolved in methanol (10 mL) and cooled to 0° C. OXONE® (2.46 g, 4 mmol) in water (10 mL) was added. After the addition, the ice bath was removed and the reaction was stirred at ambient temperature for 3 hours. The mixture was extracted with chloroform (3×50 mL). The combined organic phases were dried (MgSO$_4$) and concentrated in vacuo. The residue was purified by chromatography, affording 4-(3-fluoro-4-methoxyphenyl)-5-[4-(methylsulfonyl)phenyl]-2-(trifluoromethyl)-1H-imidazole as a solid (98 mg): m.p. 228°–234° C. (DSC, 10° C./min.). The structure assignment was supported by NMR. Mass spectrum (EI, m/e): 414. Anal. Calc'd. for $C_{18}H_{14}N_2F_4O_3S$: C, 52.17; H, 3.41; N, 6.76. Found: C, 52.30; H, 3.62; N, 6.53.

EXAMPLE 11

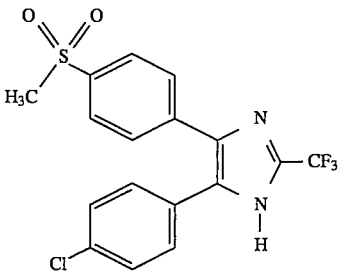

5-(4-Chlorophenyl)-4-[4-(methylsulfonyl)phenyl]-2-(trifluoromethyl)-1H-imidazole Step 1 Preparation of 4-chloro-α-[(trimethylsilyl)oxy]benzeneacetonitrile The title compound was prepared from 4-chlorobenzaldehyde (2.81 g) by the method of Example 10, step 1 (distilled at ca. 1 torr, 98°–100° C.), affording an oil (4.53 g, 94%).

Step 2 Preparation of 1-(4-chlorophenyl)-2-hydroxy-2-[4-(methylthio)phenyl]ethanone The title compound was prepared from 4-chloro-α-[(trimethylsilyl)oxy]benzeneacetonitrile from step 1 (18.9 mmol, 4.53 g) by the method of Example 10, step 2, affording a solid (3.05 g, 55%).

Step 3 Preparation of 1-(4-chlorophenyl)-2-[4-(methylthio)phenyl]ethane-1,2-dione The title compound was prepared from 1-(4-chlorophenyl)-2-hydroxy-2-[4-(methylthio)phenyl]ethanone from step 2 (4.5 mmol, 1.31 g) by the method of Example 10, step 3, affording a yellow solid (929 mg, 71%).

Step 4 Preparation of 5-(4-chlorophenyl)-4-[4-(methylthio)phenyl]-2-(trifluoromethyl)-1H-imidazole The title compound was prepared from 1-(4-chlorophenyl)-2-[4-(methylthio)phenyl]ethane-1,2-dione of step 3 (3.0 mmol, 870 mg) by the method of Example 10, step 4, affording a foam (516 mg, 47%).

Step 5 Preparation of 5-(4-chlorophenyl)-4-[4-(methylsulfonyl)phenyl]-2-(trifluoromethyl)-1H-imidazole The title compound was prepared from 4-[4-(methylthio)phenyl]-5-(4-chlorophenyl)-2-(trifluoromethyl)-1H-imidazole from step 4 (488 mg, 1.3 mmol) by the method of Example 10, step 5, affording a solid (103 mg). The structure assignment was supported by NMR. Mass spectrum (EI, m/e): 400. Anal. Calc'd. for $C_{17}H_{12}N_2ClF_3O_2S \cdot 0.5\ H_2O$: C, 49.82; H, 3.20; N, 6.84. Found: C, 49.52; H, 2.98; N, 6.46.

EXAMPLE 12

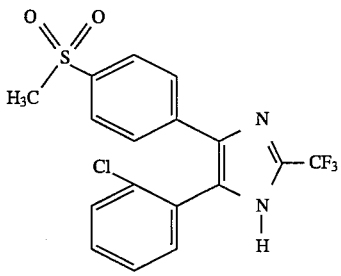

5-(2-Chlorophenyl)-4-[4-(methylsulfonyl)phenyl]-2-(trifluoromethyl)-1H-imidazole Step 1 Preparation of 2-Chloro-α-[(trimethylsilyl)oxy]benzeneacetonitrile The title compound was prepared from 2-chlorobenzaldehyde (2.81 mL) by the method of Example 10, step 1 (distilled at ca. 1 torr, 92° C.), affording an oil (5.61 g, 94%).

Step 2 Preparation of 1-(2-chlorophenyl)-2-hydroxy-2-[4-(methylthio)phenyl]ethanone The title compound was prepared from 2-chloro-α-[(trimethylsilyl)oxy]benzeneacetonitrile (23.5 mmol, 5.61 g) from step 1 by the method of Example 10, step 2, affording a solid (1.54 g, 22%).

Step 3 Preparation of 1-(2-chlorophenyl)-2-hydroxy-2-[4-(methylthio)phenyl]ethanone The title compound was prepared from 1-(2-chlorophenyl)-2-[4-(methylthio)phenyl]ethane-1,2-dione from step 2 (5.27 mmol, 1.54 g) by the method of Example 10, step 3, affording a yellow solid (374 mg, 24%).

Step 4 Preparation of 5-(2-chlorophenyl)-4-[4-(methylthio)phenyl]-2-(trifluoromethyl)-1H-imidazole The title compound was prepared from 1-(2-chlorophenyl)-2-hydroxy-2-[4-(methylthio)phenyl]ethanone from step 3 (1.27 mmol, 370 mg) by the method of Example 10, step 4, affording a white solid (291 mg, 62%). Mass spectrum (EI, m/e): 368. Anal. Calc'd. for $C_{17}H_{12}N_2ClF_3S$: C, 55.36; H, 3.28; N, 7.60. Found: C, 55.46; H, 3.13; N, 7.28.

Step 5 Preparation of 5-(2-chlorophenyl)-4-[4-(methylsulfonyl)phenyl]-2-(trifluoromethyl)-1H-imidazole 4-[4-(Methylthio)phenyl]-5-(2-chlorophenyl)-2-(trifluoromethyl)-1H-imidazole from step 4 (285 mg, 0.77 mmol) was dissolved in acetic acid (6 mL). Hydrogen peroxide (30%, 0.23 mL) was added and the solution was heated over a steam bath for 40 minutes. Lyophilization followed by chromatography afforded the title compound as a white foam (133 mg). The structure assignment was supported by NMR. Mass spectrum (EI, m/e): 400. Anal. Calc'd. for $C_{17}H_{12}N_2ClF_3O_2S$: C, 50.80; H, 2.92; N, 6.76. Found: C, 50.94; H, 3.02; N, 6.99.

EXAMPLE 13

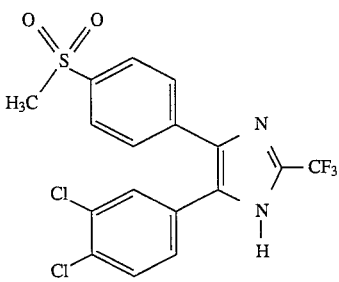

5-(3,4-Dichlorophenyl)-4-[4-(methylsulfonyl)phenyl]-2-(trifluoromethyl)-1H-imidazole Step 1 Preparation of 3,4-dichloro-α-[(trimethylsilyl)oxy]benzeneacetonitrile The title compound was prepared from 3,4-dichlorobenzaldehyde (25 mmol, 4.375 g) by the method of Example 10, step 1 (distilled at ca. 1 torr, 115° C.), affording the title compound as an oil (6.49 g, 95%).

Step 2 Preparation of 1-(3,4-dichlorophenyl)-2-hydroxy-2-[4-(methylthio)phenyl]ethanone A dry flask under an argon atmosphere containing tetrahydrofuran (50 mL) was cooled to −78° C. Lithium hexamethyldisilazide (1M in tetrahydrofuran, 25 mL) was introduced, followed by a solution of 3,4-dichloro-α-[(trimethylsilyl)oxy]benzeneacetonitrile from step 1 (23.7 mmol, 6.49 g) in tetrahydrofuran (10 mL). After 20 minutes, (4-methylthio)benzaldehyde (25 mmol, 3.33 mL) was added. The reaction was quenched after an hour by addition of 10% HCl (100 mL) and KHF$_2$ (40 mmol, 3.12 g). The mixture was stirred 45 minutes at room temperature, then extracted into ethyl acetate (200 mL). The organic phase was separated, washed with saturated NaCl solution (50 mL), then stirred for 1 hour in the presence of aqueous NaOH (1.14 g in 50 mL). The organic layer was separated, dried over MgSO$_4$, concentrated in vacuo and subjected to chromatography on silica gel (2:1 hexane/ethyl acetate), affording the title compound (2.32 g, 30%) as a waxy solid.

Step 3 Preparation of 1-(3,4-dichlorophenyl)-2-[4-(methylthio)phenyl]ethane-1,2-dione Dimethyl sulfoxide (16.3 mmol, 1.20 mL) was added to methylene chloride (70 mL) and the solution was cooled to −65° C. Trifluoroacetic acid anhydride (13.1 mmol, 1.84 mL) was added over 2 minutes and the cold solution was stirred an additional 10 minutes. A solution of 1-(3,4-dichlorophenyl)-2-hydroxy-2-[4-(methylthio)phenyl]ethanone from step 2 (7.10 mmol, 2.32 g) in methylene chloride (ca. 10 mL) was introduced and after 30 minutes, triethylamine (32.6 mmol, 4.53 mL) was added. The mixture was warmed to 0° C. over 30 minutes, diluted with water (60 mL) and extracted with ethyl acetate (200 mL). The organic phase was separated, dried over magnesium sulfate, filtered through silica gel, and concentrated in vacuo. The residue was subjected to chromatography on silica gel using mixtures of hexane and ethyl acetate as eluents, affording the title compound as a yellow solid (2.035 g, 88%).

Step 4 Preparation of 5-(3,4-dichlorophenyl)-4-[4-(methylthio)phenyl]-2-(trifluoromethyl)-1H-imidazole The title compound was prepared from 1-(3,4-dichlorophenyl)-2-[4-(methylthio)phenyl]ethane-1,2-dione from step 3 (6.26 mmol, 2.035 g) by the method of Example 10, step 4, affording a viscous oil (1.374 g, 54%).

Step 5 Preparation of 5-(3,4-dichlorophenyl)-4-[4-(methylsulfonyl)phenyl]-2-(trifluoromethyl)-1H-imidazole The title compound was prepared from 5-(3,4-dichlorophenyl)-4-[4-(methylthio)phenyl]-2-(trifluoromethyl)-1H-imidazole from step 4 (3.41 mmol, 1.374 g) by the method of Example 12, step 5, affording, after two recrystallizations from ethyl acetate and hexane, a solid (395 mg): m.p. 249°–251° (DSC, 10° C./min.). The structure assignment was supported by NMR. Anal. Calc'd. for $C_{17}H_{11}Cl_2F_3O_2S$: C, 46.91; H, 2.55; N, 6.44. Found: C, 47.15; H, 2.93; N, 5.91.

EXAMPLE 14

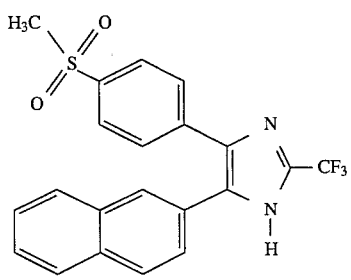

4-[4-(Methylsulfonyl)phenyl]-3-(2-naphthyl)-2-(trifluoromethyl)-1H-imidazole

Step 1 Preparation of α-[(trimethylsilyl)oxy]-2-naphthylacetonitrile

The title compound was prepared from 2-naphthaldehyde (25 mmol, 3.90 g) by the method of Example 10, step 1, (distilled at ca. 1 torr, 110° C.), affording an oil (4.896 g, 77%).

Step 2 Preparation of 2-hydroxy-2-[4-(methylthio)phenyl]-1-(2-naphthyl)ethanone

The title compound was prepared from α-[(trimethylsilyl)oxy]-2-naphthylacetonitrile from step 1 (19.2 mmol, 4.89 g) by the method of Example 13, step 2, affording a solid (3.28 g, 55%).

Step 3 Preparation of 2-[4-(methylthio)phenyl]-1-(2-naphthyl)ethane-1,2-dione

The title compound was prepared from 2-hydroxy-2-[4-(methylthio)phenyl]-1-(2-naphthyl)ethanone from step 2 above (6.50 mmol, 2.00 g) using the method of Example 10, step 3, affording a yellow solid (968 mg, 49%).

Step 4 Preparation of 4-[4-(methylthio)phenyl]-5-(2-naphthyl)-2-(trifluoromethyl)-1H-imidazole The title compound was prepared from 2-[4-(methylthio)phenyl]-1-(2-naphthyl)ethane-1,2-dione (3.14 mmol, 960 mg) from step 3 above by the method of Example 10, step 4, affording a white solid (675 mg, 56%).

Step 5 Preparation of 4-[4-(methylsulfonyl)phenyl]-5-(2-naphthyl)-2-(trifluoromethyl)-1H-imidazole The title compound was prepared from 4-[4-(methylthio)phenyl]-5-(2-naphthyl)-2-(trifluoromethyl)-1H-imidazole of step 4 above (1.77 mmol, 675 mg) by the method of Example 12, step 5, affording, after recrystallization from acetone and hexane, a solid (393 mg, 54%). The solid was diluted with acetone (ca. 1 mL) and concentrated in vacuo to remove traces of hexane: m.p. 228°–230° C. (DSC, 10° C./min.). The structure assignment was supported by NMR. Mass spectrum (EI, M/e): 416. Anal. Calc'd. for $C_{21}H_{15}F_3N_2O_2S$: C, 60.57; H, 3.63; N, 6.73. Found: C, 60.13; H, 3.97; N, 6.34.

EXAMPLE 15

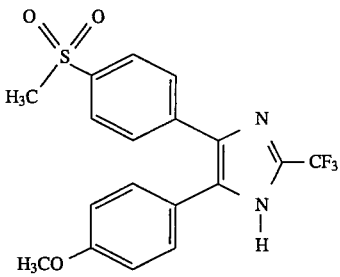

5-(4-Methoxyphenyl)-4-[4-(methylsulfonyl)phenyl]-2-(trifluoromethyl)-1H-imidazole Step 1 Preparation of 4-methoxy-α-[(trimethylsilyl)oxy] benzeneacetonitrile The title compound was prepared from p-anisaldehyde (25 mmol, 3.03 mL) by the method of Example 10, step 1 (distilled at ca. 1 torr, 102° C.), affording an oil (5.74 g, 98%).

Step 2 Preparation of 2-hydroxy-1-(4-methoxyphenyl)-2-[4-(methylthio)phenyl]ethanone The title compound was prepared from 4-methoxy-α-[(trimethylsilyl)oxy]benzeneacetonitrile from step 1 above (24.4 mmol, 5.74 g) by the method of Example 13, step 2, affording a solid (5.53 g, 79%).

Step 3 Preparation of 1-(4-methoxyphenyl)-2-[4-(methylthio)phenyl]ethane-1,2-dione The title compound was prepared from 2-hydroxy -1-(4-methoxyphenyl)-2-[4-(methylthio)phenyl]ethanone from step 2 (5.64 mmol, 1.63 g) using the method of Example 10, step 3, affording a yellow solid (968 mg, 60%).

Step 4 Preparation of 5-(4-methoxyphenyl)-4-[4-(methylthio)phenyl]-2-(trifluoromethyl)-1H-imidazole The title compound was prepared from 1-(4-methoxyphenyl)-2-[4-(methylthio)phenyl]ethane-1,2-dione from step 3 (3.33 mmol, 952 mg) by the method of Example 10, step 4, affording a viscous oil (411 mg, 34%).

Step 5 Preparation of 5-(4-methoxyphenyl)-4-[4-(methylsulfonyl)phenyl]-2-(trifluoromethyl)-1H-imidazole The title compound was prepared from 5-(4-methoxyphenyl)-4-[4-(methylthio)phenyl]-2-trifluoromethyl)-1H-imidazole from step 4 (1.12 mmol, 0.408 g) by the method of Example 12, step 5, affording, after recrystallization from ethyl acetate and hexane, a solid (236 mg, 53%). The solid was diluted with acetone (ca. 1 mL) and concentrated in vacuo to remove traces of hexane. The structure assignment was supported by NMR. Anal. Calc'd. for $C_{18}H_{15}F_3N_2O_3S$: C, 54.54; H, 3.81; N, 7.07. Found: C, 54.83; H, 3.83; N, 6.62.

EXAMPLE 16

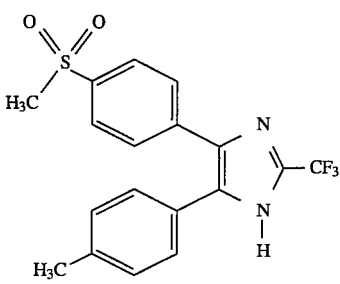

5-(4-Methylphenyl)-4-[4-(methylsulfonyl)phenyl]-2-(trifluoromethyl)-1H-imidazole Step 1 Preparation of 4-methyl-α-[(trimethylsilyl)oxy] benzeneacetonitrile The title compound was prepared from p-tolualdehyde (25 mmol, 2.94 mL) by the method of Example 10, step 1 (distilled at ca. 1 torr, 96° C.), affording an oil (5.23 g, 96%).

Step 2 Preparation of 3-hydroxy-1-(4-methylphenyl)-2-[4-(methylthio)phenyl]-ethanone The title compound was prepared from 4-methyl-α-[(trimethylsilyl)oxy]benzeneacetonitrile from step 1 (23.7 mmol, 5.20 g) by the method of Example 13, step 2, affording a solid (5.53 g, 70%).

Step 3 Preparation of 1-(4-methylphenyl)-2-[4-(methylthio)phenyl]ethane-1,2,-dione The title compound was prepared from 2-hydroxy-1-(4-methoxyphenyl)-2-[4-(methylthio)phenyl]ethanone from step 2 (5.64 mmol, 1.63 g) using the method of Example 10, step 3, affording a yellow solid (968 mg, 60%).

Step 4 Preparation of α-(4-methylphenyl)-4-[4-(methylthio)phenyl]-2-(trifluoromethyl)-1H-imidazole The title compound was prepared from 1-(4-methylphenyl)-2-[4-(methylthio)phenyl]ethane-1,2-dione from step 3 (3.29 mmol, 889 mg) by the method of Example 10, step 4, affording a viscous oil (345 mg, 30%).

Step 5 Preparation of 2-(4-methylphenyl)-4-[4-(methylsulfonyl)phenyl]-2,7-(trifluoromethyl)-1H-imidazole The title compound was prepared from 5-(4-methylphenyl)-4-[4-(methylthio)phenyl]-2-(trifluoromethyl)-1H-imidazole from step 4 (1.00 mmol, 0.345 mg) by the method of Example 12, step 5, affording, after recrystallization from acetone and hexane, a solid (95 mg, 25%): m.p. 234°–238° C. (DSC, 1.0° C./min.). The structure assignment was supported by NMR. Anal. Calc'd. for $C_{18}H_{18}F_3N_2O_2S$: C, 56.84; H, 3.97; N, 7.36. Found: C, 56.68; H, 3.98; N, 7.09.

EXAMPLE 17

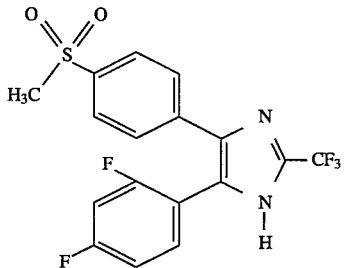

5-(2,4-Difluorophenyl)-4-[4-(methylsulfonyl)phenyl]-2-(trifluoromethyl)-1H-imidazole Step 1 Preparation of 2,4-difluoro-α-[(trimethylsilyl)oxy]benzeneacetonitrile The title compound was prepared from 2,4-difluorobenzaldehyde (25 mmol, 2.73 mL) by the method of Example 10, step 1 (distilled at ca. 1 torr, 80° C.), affording an oil (5.83 g, 97%).

Step 2 Preparation of 1-(2,4-difluorophenyl)-2-hydroxy-2-[4-(methylthio)phenyl]-ethanone The title compound was prepared from 2,4-difluoro-α-[(trimethylsilyl)oxy]benzeneacetonitrile from step 1 (24.2 mmol, 5.85 g) by the method of Example 13, step 2, affording a solid (3.63 g, 51%).

Step 3 preparation of 1-(2,4-difluorophenyl)-2-[4-(methylthio)phenyl]ethane-1,2-dione The title compound was prepared from 1-(2,4-difluorophenyl)-2-hydroxy-2-[4-(methylthio)phenyl]-ethanone from step 2 (12.3 mmol, 3.63 g) using the method of Example 10, step 3, affording a yellow solid (1.57 g, 44%).

Step 4 Preparation of 5-(2,4-difluorophenyl)-4-[4-(methylthio)phenyl]-2-(trifluoromethyl)-1H-imidazole The title compound was prepared from 1-(2,4-difluorophenyl)-2-[4-(methylthio)phenyl]ethane-1,2-dione from step 3 (5.38 mmol, 1.57 g) by the method of Example 10, step 4, affording a viscous oil (938 mg, 47%).

Step 5 Preparation of 5-(2,4-difluorophenyl)-4-[4-(methylsulfonyl)phenyl]-2-(trifluoromethyl)-1H-imidazole The title compound was prepared from 5-(2,4-difluorophenyl)-4-[4-(methylthio)phenyl]-2-(trifluoromethyl)-1H-imidazole from step 4 (2.53 mmol, 0.938 g) by the method of Example 12, step 5, affording, after recrystallization from ethyl acetate and hexane, a solid (487 mg, 48%). The solid was diluted with acetone (ca. 1 mL) and concentrated in vacuo to remove traces of hexane. The structure assignment was supported by NMR. Mass Spectrum (EI, M/e): 402. Anal. Calc'd. for $C_{17}H_{11}F_5O_2S$: C, 50.75; H, 2.76; N, 6.96. Found: C, 50.83; H, 2.59; N, 6.79.

EXAMPLE 18

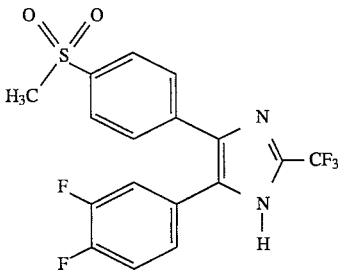

5-(3,4-Difluoro]phenyl)-4-[4-(methylsulfonyl)phenyl]-2-(trifluoromethyl)-1H-imidazole Step 1 Preparation of 3,4-difluoro-α-[(trimethylsilyl)oxy]benzeneacetonitrile The title compound was prepared from 3,4-difluorobenzaldehyde (25 mmol, 2.73 mL) by the method of Example 10, step 1 (distilled at ca. 1 torr, 80° C.), affording an oil (6.02 g, 100%).

Step 2 Preparation of 1-(3,4-difluorophenyl)-2-hydroxy-2-[4-(methylthio)phenyl]-ethanone The title compound was prepared from 3,4-difluoro-α-[(trimethylsilyl)oxy]benzeneacetonitrile from step 1 above (25 mmol, 6.02 g) by the method of Example 13, step 2, affording a solid (1.83 g, 25%).

Step 3 Preparation of 1-(3,4-difluorophenyl)-2-[4-(methylthio)phenyl]ethane-1,2-dione The title compound was prepared from 1-(3,4-difluorophenyl)-2-hydroxy-2-[4-(methylthio)phenyl]-ethanone from step 2 (6.23 mmol, 1.83 g) using the method of Example 10, step 3, affording a yellow solid (985 g, 54%).

Step 4 Preparation of 5-(3,4-difluorophenyl)-4-[4-(methylthio)phenyl-2-(trifluoromethyl)-1H-imidazole The title compound was prepared from 1-(3,4-difluorophenyl)-2-[4-(methylthio)phenyl]ethane-1,2-dione from step 3 (3.37 mmol, 985 mg) by the method of Example 10, step 4, affording a viscous oil (606 mg, 49%).

Step 5 Preparation of 5-(3,4-difluorophenyl)-4-[4-(methylsulfonyl)phenyl]-2-(trifluoromethyl)-1H-imidazole The title compound was prepared from 5-(3,4-difluorophenyl)-4-[4-(methylthio)phenyl]-2-(trifluoromethyl)-1H-imidazole from step 4 (1.64 mmol, 0.606 g) by the method of Example 12, step 5, affording, after recrystallization from acetone, a solid (313 mg, 47%). The solid was diluted with acetone (ca. 1 mL) and concentrated in vacuo to remove traces of hexane: m.p. 249°–252° C. (DSC, 10° C./min.). The structure assignment was supported by NMR. Anal. Calc'd. for $C_{17}H_{11}F_5O_2S$: C, 50.75; H, 2.76; N, 6.96. Found: C, 50.58; H, 2.96; N, 6.66.

EXAMPLE 19

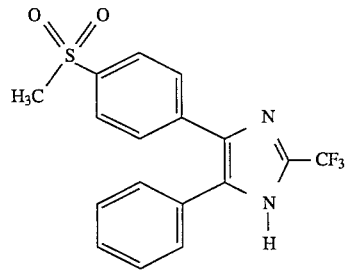

4-[4-(Methylsulfonyl)phenyl]-5-phenyl-2-(trifluoromethyl)-1H-imidazole

Step 1 Preparation of α-(trimethylsilyl)oxy]benzeneacetonitrile

The title compound was prepared from benzaldehyde (25 mmol, 2.55 mL) by the method of Example 10, step 1 (distilled at ca. 1 torr, 86° C.), affording an oil (4.52 g, 88%).

Step 2 Preparation of 2-hydroxy-2-[4-(methylthio)phenyl)]-1-phenyl-ethanone

The title compound was prepared from α-(trimethylsilyl)oxy]benzeneacetonitrile from step 1 (22 mmol, 4.52 g) by the method of Example 13, step 2, affording a solid (3.25 g, 57%).

Step 3 Preparation of 2-[4-(methylthio)phenyl]-1(phenyl)ethane-1,2-dione

The title compound was prepared from 2-hydroxy-2-[4-(methylthio)phenyl]-1-phenyl-ethanone from step 2 (12.6 mmol, 3.25 g) using the method of Example 10, step 3, affording a yellow solid (1.50 g, 46%).

Step 4 Preparation of 4-[4-(methylthio)phenyl]-5-phenyl-2-(trifluoromethyl)-1H-imidazole The title compound was prepared from 2-[4-(methylthio)phenyl]-1-(phenyl)ethane-1,2-dione from step 3 (5.87 mmol, 1.50 g) by the method of Example 10, step 4, affording a viscous oil (918 mg, 47%).

Step 5 Preparation of 4-[4-(methylsulfonyl)phenyl]-5-phenyl-2-(trifluoromethyl)-1H-imidazole The title compound was prepared from 4-[4-(methylthio)phenyl]-5-phenyl-2-(trifluoromethyl)-1H-imidazole from step 4 (2.75 mmol, 0.918 g) by the method of Example 12, step 5, affording, after recrystallization from acetone, a solid (489 mg, 45%). The solid was diluted with acetone (ca. 1 mL) and concentrated in vacuo to remove traces of hexane: m.p. 228°–230° C. (DSC, 10° C./min.). The structure assignment was supported by NMR. Mass spectrum (EI, M/e): 366. Anal. Calc'd. for $C_{17}H_{12}F_3O_2S$: C, 55.73; H, 3.58; N, 7.65. Found: C, 55.58; H, 3.66; N, 7.31.

EXAMPLE 20

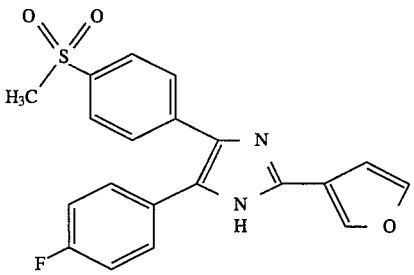

5-(4-Fluorophenyl)-2-(3-furyl)-4-(4-methylsulfonylphenyl)-1H-imidazole

In a manner similar to Example 1, Method A, 1-(4-methylsulfonylphenyl)-2-(4-fluorophenyl)-ethane-1,2-dione (Example 1, Method A, step 4) (1 g, 3.3 mmol), ammonium acetate (2 g, 25.9 mmol), 3-furaldehyde (350 mg, 3.64 mmol) and acetic acid (20 ml) gave 500 mg (47%) product after recrystallization from ethanol and water. m.p. 233°–235° C. (decomp..). Anal. Calc'd. for $C_{20}H_{18}N_2O_3FS$ (M.W. 382.42): C, 62.82; H, 3.95; N, 7.33; S, 8.38. Found: C, 62.50; H, 3.90; N, 7.04; S, 8.25.

EXAMPLE 21

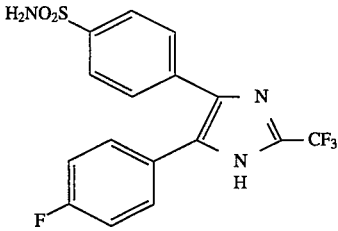

4-[5-(4-Fluorophenyl)-2-(trifluoromethyl)-1H-imidazol-4-yl]benzenesulfonamide

Step 1 Preparation of 5-(4-fluorophenyl-4-(4-methylsulfonylphenyl)-2-trifluoromethyl-1-(2-trimethylsilylethoxymethyl)-1H-imidazole A mixture of hexane-washed sodium hydride (NaH) (110 mg of 60%, 2.8 mmol) in dimethylformamide (DMF) (15 mL) was stirred under a nitrogen atmosphere at 25° C. and a solution of 5-(4-fluorophenyl)-4-(4-methylsulfonylphenyl)-2-trifluoromethyl-1H-imidazole (Example 1) (970 mg, 2.5 mmol) in DMF (5 ml) was added over 15 minutes. This mixture was stirred an additional 30 minutes. Trimethylsilylethoxymethyl chloride (450 mg, 3 mmol) was added and the reaction mixture was stirred for 16 hours at 25° C. The reaction mixture was poured into 2% aqueous $NH_4Cl$ (150 mL) and extracted with ethyl acetate. After drying ($Na_2SO_4$) and solvent removal, the protected sulfone imidazole (1.1 g, 95%) was essentially pure and was used without further purification.

Step 2 Preparation of 4-[5-(4-fluorophenyl)-2-trifluoromethyl-1-(2-trimethylsilylethoxymethyl)-1H-imidazol-4-yl]benzanesulfomide To a solution of the protected sulfone imidazole from step 1 (1.1 g, 2.0 mmol) in THF (15 mL) at 0° C. under an argon atmosphere, n-butyl magnesium bromide (n-BuMgBr) (2M solution in THF, 4.5 mL) was added and the temperature warmed to 25° C. over 30 minutes. Triethylborane ($Et_3B$) (1M solution in THF, 9 mL) was added and the reaction was heated to reflux for 48 hours. The reaction mixture was cooled to 25° C. and a mixture of hydroxylamine-O-sulfonic acid ($NH_2OSO_3H$) (2 g) and sodium acetate (2 g) in water (8 mL) was added and rapidly stirred at 25° C. for 16 hours. Water (50 mL) was added and the product was extracted with ethyl acetate, dried ($Na_2SO_4$), and evaporated. The residue was chromatographed on silica gel using mixtures of ethyl acetate and toluene as the eluent to give 500 mg (45%) of the desired protected sulfonamide. The product was used directly in the next step.

Step 3 Preparation of 4-[5-(4-fluorophenyl-2-trifluoromethyl-1H-imidazol-4-yl]benzenesulfonamide A solution of protected sulfonamide from step 2 (500 mg, 1 mmol) in a solution of 3N HCl (5 mL) in EtOH (4 mL) was heated to reflux for 1 hour, cooled and diluted with water (20 mL). The resulting mixture was extracted with methylene chloride, dried ($Na_2SO_4$) and the solvent was evaporated. The residue was recrystallized from toluene containing a small amount of ethyl acetate to give the title product (150 mg, 40%): m.p. 259°–260° C. Anal. Calc'd. for $C_{16}H_{11}N_3O_2F_4S$: C, 49.87; H, 2.88; N, 10.90; S, 8.32. Found: C, 50.30; H, 3.10; N, 10.55; S, 8.73.

The following imidazole derivatives could be prepared by the procedure described in Example 21:

EXAMPLE 22

4-[5-(4-fluorophenyl)-2-phenoxymethyl-1H-imidazol-4-yl]benzenesulfonamide;

EXAMPLE 23

4-[5-(4-fluorophenyl)-2-(2-phenyl-trans-eth-1-ene)-1H-imidazol-4-yl]benzenesulfonamide;

EXAMPLE 24

4-[2-(2-benzofuryl)-5-(4-fluorophenyl)-1H-imidazol-4-yl]benzenesulfonamide;

EXAMPLE 25

4-[5-(4-fluorophenyl)-2-isopropyl-1H-imidazol-4-yl]benzenesulfonamide;

EXAMPLE 26

4-[5-(4-fluorophenyl)-2-methyl-1H-imidazol-4-yl]benzenesulfonamide;

EXAMPLE 27

4-[5-(4-fluorophenyl)-2-(2-furyl)-1H-imidazol-4-yl]benzenesulfonamide;

EXAMPLE 28

4-[2-benzylthio-5-(4-fluorophenyl)-1H-imidazol-4-yl]benzenesulfonamide;

EXAMPLE 29

4-[5-(4-fluorophenyl)-2-hydroxymethyl-1H-imidazol-4-yl]benzenesulfonamide;

EXAMPLE 30

4-[5-(3-fluoro-4-methoxyphenyl)-2-(trifluoromethyl)-1H-imidazol-4-yl]benzenesulfonamide

EXAMPLE 31

4-[5-(4-chlorophenyl)-2-(trifluoromethyl)-1H-imidazol-4-yl]benzenesulfonamide;

EXAMPLE 32

4-[5-(2-chlorophenyl)-2-(trifluoromethyl)-1H-imidazol-4-yl]benzenesulfonamide;

EXAMPLE 33

4-[5-(3,4-dichlorophenyl)-2-(trifluoromethyl)-1H-imidazol-4-yl]benzenesulfonamide;

EXAMPLE 34

4-[5-(2-naphthyl)-2-(trifluoromethyl)-1H-imidazol-4-yl]benzenesulfonamide;

EXAMPLE 35

4-[5-(4-methoxyphenyl)-2-(trifluoromethyl)-1H-imidazol-4-yl]benzenesulfonamide;

EXAMPLE 36

4-[5-(4-methylphenyl)-2-(trifluoromethyl)-1H-imidazol-4-yl]benzenesulfonamide;

EXAMPLE 37

4-[5-(2,4-difluorophenyl)-2-(trifluoromethyl)-1H-imidazol-4-yl]benzenesulfonamide;

EXAMPLE 38

4-[5-(3,4-difluorophenyl)-2-(trifluoromethyl)-1H-imidazol-4-yl]benzenesulfonamide;

EXAMPLE 39

4-[5-phenyl-2-(trifluoromethyl)-1H-imidazol-4-yl]benzenesulfonamide; and

EXAMPLE 40

4-[5-(4-fluorophenyl)-2-(3-furyl)-1H-imidazol-4-yl]benzenesulfonamide.

BIOLOGICAL EVALUATION

Rat Carrageenan Foot Pad Edema Test

The carrageenan foot edema test was performed with materials, reagents and procedures essentially as described by Winter, et al., (*Proc. Soc. Exp. Biol. Med.*, 111, 544 (1962)). Male Sprague-Dawley rats were selected in each group so that the average body weight was as close as possible. Rats were fasted with free access to water for over sixteen hours prior to the test. The rats were dosed orally (1 mL) with compounds suspended in vehicle containing 0.5% methylcellulose and 0.025% surfactant, or with vehicle alone. One hour later a subplantar injection of 0.1 mL of 1% solution of carrageenan/sterile 0.9% saline was administered and the volume of the injected foot was measured with a displacement plethysmometer connected to a pressure transducer with a digital indicator. Three hours after the injection of the carrageenan, the volume of the foot was again measured. The average foot swelling in a group of drug-treated animals was compared with that of a group of placebo-treated animals and the percentage inhibition of edema was determined (Otterness and Bliven, *Laboratory Models for Testing NSAIDs*, in Non-steroidal Anti-Inflammatory Drugs, (J. Lombardino, ed. 1985)). The % inhibition shows the % decrease from control paw volume determined in this procedure and the data for selected compounds in this invention are summarized in Table I.

Rat Carrageenan-induced Analgesia Test

The analgesia test using rat carrageenan was performed with materials, reagents and procedures essentially as described by Hargreaves, et al., (*Pain*, 32, 77 (1988)). Male Sprague-Dawley rats were treated as previously described for the Carrageenan Foot Pad Edema test. Three hours after the injection of the carrageenan, the rats were placed in a special plexiglass container with a transparent floor having a high intensity lamp as a radiant heat source, positionable under the floor. After an initial twenty minute period, thermal stimulation was begun on either the injected foot or on the contralateral uninjected foot. A photoelectric cell turned off the lamp and timer when light was interrupted by paw withdrawal. The time until the rat withdraws its foot was then measured. The withdrawal latency in seconds was determined for the control and drug-treated groups, and percent inhibition of the hyperalgesic foot withdrawal determined. Results are shown in Table I.

TABLE I

|  | RAT PAW EDEMA<br>% Inhibition[1] | ANALGESIA<br>% Inhibition[1] |
|---|---|---|
| Example 1 | 22 | 25 |

[1] @ 30 mg/kg body weight

Evaluation of COX I and COX II activity in vitro

The compounds of this invention exhibited inhibition in vitro of COX II. The COX II inhibition activity of the compounds of this invention illustrated in the Examples was determined by the following methods.

a. Preparation of Recombinant COX Baculoviruses

A 2.0 kb fragment containing the coding region of either human or murine COX-I or human or murine COX-II was cloned into a BamH1 site of the baculovirus transfer vector pVL1393 (Invitrogen) to generate the baculovirus transfer vectors for COX-I and COX-II in a manner similar to the method of D. R. O'Reilly et al (*Baculovirus Expression Vectors: A Laboratory Manual* (1992)). Recombinant baculoviruses were isolated by transfecting 4 µg of baculovirus transfer vector DNA into SF9 insect cells (2×10e8) along with 200 ng of linearized baculovirus plasmid DNA by the calcium phosphate method. See M. D. Summers and G. E. Smith, *A Manual of Methods for Baculovirus Vectors and Insect Cell Culture Procedures*, Texas Agric. Exp. Station Bull. 1555 (1987). Recombinant viruses were purified by three rounds of plaque purification and high titer (10E7–10E8 pfu/ml) stocks of virus were prepared. For large scale production, SF9 insect cells were infected in 10 liter fermentors ($0.5 \times 10^6$/ml) with the recombinant baculovirus stock such that the multiplicity of infection was 0.1. After 72 hours the cells were centrifuged and the cell pellet homogenized in Tris/Sucrose (50 mM: 25%, pH 8.0) containing 1% 3-[(3-cholamidopropyl)dimethylammonio]-1-propanesulfonate (CHAPS). The homogenate was centrifuged at 10,000×G for 30 minutes, and the resultant supernatant was stored at −80° C. before being assayed for COX activity.

b. Assay for COX I and COX II Activity

COX activity was assayed as $PGE_2$ formed/µg protein/time using an ELISA to detect the prostaglandin released. CHAPS-solubilized insect cell membranes containing the appropriate COX enzyme were incubated in a potassium phosphate buffer (50 mM, pH 8.0) containing epinephrine, phenol, and heme with the addition of arachidonic acid (10 µM). Compounds were pre-incubated with the enzyme for 10–20 minutes prior to the addition of arachidonic acid. Any reaction between the arachidonic acid and the enzyme was stopped after ten minutes at 37° C./room temperature by transferring 40 µl of reaction mix into 160 µl ELISA buffer and 25 µM indomethacin. The $PGE_2$ formed was measured by standard ELISA technology (Cayman Chemical). Results are shown in Table II.

TABLE II

| Example | Human COX II<br>$ID_{50}$ µM | Human COX I<br>$ID_{50}$ µM |
|---|---|---|
| 1 | .2 | >100 |
| 2 | .2 | >100 |
| 3 | .2 | 2.2 |
| 4 | .5 | >100 |
| 5 | 1.2 | >100 |
| 6 | 4.6 | >100 |
| 7 | 4.8 | >100 |
| 8 | <.1 | 2.1 |
| 9 | 5.1 | >100 |
| 10 | 1.2 | 63.5 |
| 11 | .4 | 10.4 |
| 12 | 1.3 | >100 |
| 13 | <.1 | 9.6 |
| 14 | .6 | 2.0 |
| 15 | 2.9 | 5.6 |
| 16 | .6 | 20 |
| 17 | .3 | >100 |
| 18 | .2 | >100 |
| 19 | .5 | >100 |
| 20 | 40.7 | >100 |
| 21 | <.1 | 10.8 |

Also embraced within this invention is a class of pharmaceutical compositions comprising one or more compounds of Formula I in association with one or more non-toxic, pharmaceutically-acceptable carriers and/or diluents and/or adjuvants (collectively referred to herein as "carrier" materials) and, if desired, other active ingredients. The compounds of the present invention may be administered by any suitable route, preferably in the form of a pharmaceutical composition adapted to such a route, and in a dose effective for the treatment intended. The compounds and composition may, for example, be administered intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. The active ingredient may also be administered by injection as a composition wherein, for example, saline, dextrose or water may be used as a suitable carrier.

The amount of therapeutically active compound that is administered and the dosage regimen for treating a disease condition with the compounds and/or compositions of this invention depends on a variety of factors, including the age, weight, sex and medical condition of the subject, the severity of the disease, the route and frequency of administration, and the particular compound employed, and thus may vary widely. The pharmaceutical compositions may contain active ingredient in the range of about 0.1 to 2000 mg, preferably in the range of about 0.5 to 500 mg and most preferably between about 1 and 100 mg. A daily dose of about 0.01 to 100 mg/kg body weight, preferably between about 0.1 and about 50 mg/kg body weight and most preferably between about 1 to 20 mg/kg body weight, may be appropriate. The daily dose can be administered in one to four doses per day.

For therapeutic purposes, the compounds of this invention are ordinarily combined with one or more adjuvants appropriate to the indicated route of administration. If administered per os, the compounds may be admixed with lactose, sucrose, search powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations.

What is claimed is:

1. A compound of Formula I

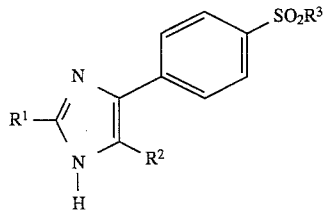

I wherein $R^1$ is selected from alkyl, haloalkyl, aralkyl, acyl, cyano, alkoxy, alkylthio, alkylthioalkyl, alkylsulfonyl, haloalkylsulfonyl, arylsulfonyl, halo, hydroxyalkyl, alkylcarbonyl, arylcarbonyl, aralkylcarbonyl, cyanoalkyl, aralkenyl, aminoalkyl, alkylaminoalkyl, N-arylaminoalkyl, N-alkyl-N-aryl-aminoalkyl, carboxyalkyl, alkoxycarbonylalkyl, alkoxycarbonyl, haloalkylcarbonyl, carboxyl, alkoxyalkyl, aminocarbonyl, alkylaminocarbonyl, alkylaminocarbonylalkyl, aralkoxy, aralkylthio, arylthioalkyl, aryloxyalkyl, haloaryloxyalkyl, arylthio, aryloxy, aralkylthioalkyl, aralkoxyalkyl, alkoxyaralkoxyalkyl and aryl optionally substituted at a substitutable position with one or more radicals selected from halo, alkylthio, alkylsulfinyl, alkyl, cyano, haloalkyl, hydroxyl, alkoxy, hydroxyalkyl and haloalkoxy;

wherein $R^2$ is aryl optionally substituted with one or more radicals selected from halo, alkylthio, alkylsulfinyl, alkyl, cyano, carboxyl, alkoxycarbonyl, haloalkyl, hydroxyl, alkoxy, hydroxyalkyl, alkoxyalkyl, haloalkoxy, amino, alkylamino, arylamino and nitro; and wherein $R^3$ is amino;

or a pharmaceutically-acceptable salt thereof.

2. A compound of claim 1 wherein $R^1$ is selected from lower alkyl, lower haloalkyl, lower aralkyl, formyl, cyano, lower alkoxy, lower alkylthio, lower alkylthioalkyl, lower alkylsulfonyl, lower haloalkylsulfonyl, lower arylsulfonyl, halo, lower hydroxyalkyl, lower alkoxyalkyl, lower alkylcarbonyl, lower arylcarbonyl, lower aralkylcarbonyl, lower cyanoalkyl, lower aralkenyl, lower aminoalkyl, lower alkylaminoalkyl, lower N-arylaminoalkyl, lower N-alkyl-N-arylaminoalkyl, lower carboxyalkyl, lower alkoxycarbonylalkyl, lower alkoxycarbonyl, lower haloalkylcarbonyl, carboxyl, aminocarbonyl, lower alkylaminocarbonyl, lower alkylaminocarbonylalkyl, lower aralkoxy, lower aralkylthio, lower arylthioalkyl, lower aryloxyalkyl, lower haloaryloxyalkyl, arylthio, aryloxy, lower aralkylthioalkyl, lower aralkoxyalkyl, lower alkoxyaralkoxyalkyl, and aryl, wherein the aryl radicals are optionally substituted at a substitutable position with one or more radicals selected from halo, lower alkylthio, lower alkylsulfinyl, lower alkyl, cyano, lower haloalkyl, lower hydroxyl, lower alkoxy, lower hydroxyalkyl and lower haloalkoxy; wherein $R^2$ is aryl optionally substituted with one or more radicals selected from halo, lower alkylthio, lower alkylsulfinyl, lower alkyl, cyano, carboxyl, lower alkoxycarbonyl, lower haloalkyl, hydroxyl, lower alkoxy, lower hydroxyalkyl, lower alkoxyalkyl, lower haloalkoxy, amino, lower alkylamino, arylamino and nitro; and wherein $R^3$ is amino; or a pharmaceutically-acceptable salt thereof.

3. A compound of claim 2 wherein $R^1$ is selected from methyl, ethyl, propyl, isopropyl, butyl, isobutyl, tert-butyl, pentyl, hexyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, benzyl, phenylethyl, methoxybenzyloxymethyl, chlorophenoxymethyl, hydroxymethyl, 2-phenylethenyl, phenylcarbonyl, benzylthio, benzyloxy, phenoxymethyl, and phenylthiomethyl; wherein $R^2$ is selected from phenyl, and naphthyl, wherein the phenyl, and naphthyl radicals are optionally substituted at a substitutable position with one or more radicals selected from fluoro, chloro, bromo, iodo, methyl, ethyl, isopropyl, butyl, isobutyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, methoxy, ethoxy, isopropoxy, tert-butoxy, propoxy, butoxy, isobutoxy, pentoxy, amino, trifluoromethoxy, cyano, carboxyl, methoxycarbonyl, ethoxycarbonyl, isopropoxycarbonyl, tert-butoxycarbonyl, propoxycarbonyl, butoxycarbonyl, isobutoxycarbonyl, pentoxycarbonyl, hydroxyl, nitro, methylsulfinyl, butylsulfinyl, hydroxymethyl, methoxymethyl, ethoxymethyl, methylamino, phenylamino, methylthio, ethylthio, propylthio and butylthio; or a pharmaceutically-acceptable salt thereof.

4. A compound of claim 3 selected from compounds, or their pharmaceutically acceptable salts, of the group consisting of 4-[5-(3-chlorophenyl)-2-trifluoromethyl-1H-imidazol-4-yl]benzenesulfonamide;

4-[5-(3-chloro-4-methylphenyl)-2-trifluoromethyl-1H-imidazol-4-yl]benzenesulfonamide;

4-[5-(3-fluorophenyl)-2-trifluoromethyl-1H-imidazol-4-yl]benzenesulfonamide;

4-[5-(3-chloro-4-methoxyphenyl)-2-trifluoromethyl-1H-imidazol-4-yl]benzenesulfonamide;

4-[5-(2,4-dichlorophenyl)-2-trifluoromethyl-1H-imidazol-4-yl]benzenesulfonamide;

4-[5-(4-bromophenyl)-2-trifluoromethyl-1H-imidazol-4-yl]benzenesulfonamide;

4-[2-trifluoromethyl-5-(4-trifluoromethylphenyl)-1H-imidazol-4-yl]benzenesulfonamide;

4-[2-trifluoromethyl -5-(4-trifluoromethoxyphenyl)-1H-imidazol-4-yl]benzenesulfonamide;

4-[5-(4-ethylphenyl)-2-trifluoromethyl-1H-imidazol-4-yl]benzenesulfonamide;

4-[5-(4-butylphenyl)-2-trifluoromethyl-1H-imidazol-4-yl]benzenesulfonamide;

4-[5-(4-butoxyphenyl)-2-trifluoromethyl-1H-imidazol-4-yl]benzenesulfonamide;

4-[5-(4-methylthiophenyl)-2-trifluoromethyl-1H-imidazol-4-yl]benzenesulfonamide;

4-[5-(3,5-dichloro-4-methoxyphenyl)-2-trifluoromethyl -1H-imidazol-4-yl]benzenesulfonamide;

5-(3,5-dichloro-4-methylphenyl)-2-trifluoromethyl-1H-imidazol-4-yl]benzenesulfonamide;

4-[2-(4-chlorophenoxy)methyl-5-(4-chlorophenyl)-1H-imidazol-4-yl]benzenesulfonamide;

4-[5-(4-chlorophenyl)-2-[(4-fluorophenoxy)methyl]-1H-imidazol-4-yl]benzenesulfonamide;

4-[5-(4-chlorophenyl)-2-(phenylthiomethyl)-1H-imidazol-4-yl]benzenesulfonamide;

4-[5-(4-chlorophenyl)-2-[(4-methoxybenzyloxy)methyl]-1H-imidazol-4-yl]benzenesulfonamide;

4-[2-benzyl-5-(4-chlorophenyl)-1H-imidazol-4-yl]benzenesulfonamide;

4-[5-(4-chlorophenyl)-2-(phenylethyl)-1H-imidazol-4-yl]benzenesulfonamide;

4-[5-(4-chlorophenyl)-2-(phenylcarbonyl)-1H-imidazol-4-yl]benzenesulfonamide;

4-[5-(4-chlorophenyl)-2-phenoxymethyl-1H-imidazol-4-yl]benzenesulfonamide;

4-[5-(4-chlorophenyl)-2-(2-phenyl-trans-eth-1-ene)-1H-imidazol-4-yl]benzenesulfonamide;

4-[2-benzylthio-5-(4-chlorophenyl)-1H-imidazol-4-yl]benzenesulfonamide;

4-[5-(4-chlorophenyl)-2-(trifluoromethyl)-1H-imidazol-4-yl]benzenesulfonamide;

4-[5-phenyl-2-phenoxymethyl-1H-imidazol-4-yl]benzenesulfonamide;

4-[5-phenyl-2-(2-phenyl-trans-eth-1-ene)-1H-imidazol-4-yl]benzenesulfonamide;

4-[2-benzylthio-5-phenyl-imidazol-4-yl]benzenesulfonamide;

4-[5-phenyl-2-(trifluoromethyl)-1H-imidazol-4-yl]benzenesulfonamide;

4-[5-(4-fluorophenyl)-2-(trifluoromethyl)-1H-imidazol-4-yl]benzenesulfonamide;

4-[5-(4-fluorophenyl)-2-phenoxymethyl -1H-imidazol-4-yl]benzenesulfonamide;

4-[5-(4-fluorophenyl)-2-(2-phenyl-trans-eth-1-ene)-1H-imidazol-4-yl]benzenesulfonamide;

4-[5-(4-fluorophenyl)-2-isopropyl-1H-imidazol-4-yl]benzenesulfonamide;

4-[5-(4-fluorophenyl)-2-methyl-1H-imidazol-4-yl]benzenesulfonamide;

4-[2-benzylthio-5-(4-fluorophenyl)-1H-imidazol-4-yl]benzenesulfonamide;

4-[5-(4-fluorophenyl)-2-hydroxymethyl -1H-imidazol-4-yl]benzenesulfonamide;

4-[5-(3-fluoro-4-methoxyphenyl)-2-(trifluoromethyl)-1H-imidazol-4-yl]benzenesulfonamide;

4-[5-(4-chlorophenyl)-2-(trifluoromethyl)-1H-imidazol-4-yl]benzenesulfonamide;

4-[5-(2-chlorophenyl)-2-(trifluoromethyl)-1H-imidazol-4-yl]benzenesulfonamide;

4-[5-(3,4-dichlorophenyl)-2-(trifluoromethyl)-1H-imidazol-4-yl]benzenesulfonamide;

4-[5-(2-naphthyl)-2-(trifluoromethyl)-1H-imidazol-4-yl]benzenesulfonamide;

4-[5-(4-methoxyphenyl)-2-(trifluoromethyl)-1H-imidazol-4-yl]benzenesulfonamide;

4-[5-(4-methylphenyl)-2-(trifluoromethyl)-1H-imidazol-4-yl]benzenesulfonamide;

4-[5-(2,4-difluorophenyl)-2-(trifluoromethyl)-1H-imidazol-4-yl]benzenesulfonamide;

4-[5-(3,4-difluorophenyl)-2-(trifluoromethyl)-1H-imidazol-4-yl]benzenesulfonamide; and 4-[5-phenyl-2-(trifluoromethyl)-1H-imidazol-4-yl]benzenesulfonamide.

5. A compound of Formula II

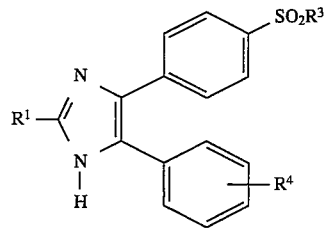

wherein $R^1$ is selected from lower alkyl, lower haloalkyl, lower hydroxyalkyl, lower aralkenyl, lower aryloxyalkyl, and lower arylthioalkyl; wherein $R^3$ is amino; and wherein $R^4$ is one or more radicals selected from hydrido, halo, lower alkyl and lower alkoxy; or a pharmaceutically-acceptable salt thereof.

6. A compound of claim 5 wherein $R^1$ is selected from methyl, ethyl, propyl, isopropyl, butyl, isobutyl, tert-butyl, pentyl, hexyl, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl, dichloropropyl, hydroxymethyl, 2-phenylethenyl, phenoxymethyl, and phenylthiomethyl; wherein $R^3$ is amino; and wherein $R^4$ is one or more radicals selected from hydrido, fluoro, chloro, bromo, methyl, ethyl, propyl, isopropyl, butyl, isobutyl, tert-butyl, methoxy, ethoxy, propoxy and n-butoxy; or a pharmaceutically-acceptable salt thereof.

7. A pharmaceutical composition comprising a therapeutically-effective amount of a compound, said compound selected from a family of compounds of claim 1; or a pharmaceutically-acceptable salt thereof.

8. A pharmaceutical composition comprising a therapeutically-effective amount of a compound, said compound selected from a family of compounds of claim 2; or a pharmaceutically-acceptable salt thereof.

9. A pharmaceutical composition comprising a therapeutically-effective amount of a compound, said compound selected from a family of compounds of claim 3; or a pharmaceutically-acceptable salt thereof.

10. A pharmaceutical composition comprising a therapeutically-effective amount of a compound, said compound selected from a family of compounds of claim 4; or a pharmaceutically-acceptable salt thereof.

11. A pharmaceutical composition comprising a therapeutically-effective amount of a compound, said compound selected from a family of compounds of claim 5; or a pharmaceutically-acceptable salt thereof.

12. A pharmaceutical composition comprising a therapeutically-effective amount of a compound, said compound selected from a family of compounds of claim 6; or a pharmaceutically-acceptable salt thereof.

13. A method of treating inflammation or an inflammation-associated disorder in a subject, said method comprising administering to the subject having such inflammation or inflammation-associated disorder, a therapeutically-effective amount of a compound of claim 1; or a pharmaceutically-acceptable salt thereof.

14. A method of treating inflammation or an inflammation-associated disorder in a subject, said method comprising administering to the subject having such inflammation or inflammation-associated disorder, a therapeutically-effective amount of a compound of claim 2; or a pharmaceutically-acceptable salt thereof.

15. A method of treating inflammation or an inflammation-associated disorder in a subject, said method comprising administering to the subject having such inflammation or inflammation-associated disorder, a therapeutically-effective amount of a compound of claim 3; or a pharmaceutically-acceptable salt thereof.

16. A method of treating inflammation or an inflammation-associated disorder in a subject, said method comprising administering to the subject having such inflammation or inflammation-associated disorder, a therapeutically-effective amount of a compound of claim 4; or a pharmaceutically-acceptable salt thereof.

17. A method of treating inflammation or an inflammation-associated disorder in a subject, said method comprising administering to the subject having such inflammation or inflammation-associated disorder, a therapeutically-effective amount of a compound of claim 5; or a pharmaceutically-acceptable salt thereof.

18. A method of treating inflammation or an inflammation-associated disorder in a subject, said method comprising administering to the subject having such inflammation or inflammation-associated disorder, a therapeutically-effective amount of a compound of claim 6; or a pharmaceutically-acceptable salt thereof.

19. The method of claim 13 for treatment of inflammation.

20. The method of claim 13 for treatment of an inflammation-associated disorder.

21. The method of claim 20 wherein the inflammation-associated disorder is arthritis.

22. The method of claim 20 wherein the inflammation-associated disorder is pain.

23. The method of claim 20 wherein the inflammation-associated disorder is fever.

\* \* \* \* \*